US012622986B2

(12) United States Patent
Dunn et al.

(10) Patent No.: US 12,622,986 B2
(45) Date of Patent: May 12, 2026

(54) METHOD OF STERILIZING WASTE CONTAINERS WITH ULTRAVIOLET LIGHT

(71) Applicant: Munchkin, Inc., Van Nuys, CA (US)

(72) Inventors: Steven Bryan Dunn, Beverly Hills, CA (US); Thomas Edward Birkert, West Hills, CA (US); Kevin Douglas Johnson, Tarzana, CA (US); Michael John Laudi, Los Angeles, CA (US); Nicholas Arthur Trumbo, Valencia, CA (US); Sung Yun Chan, Pasadena, CA (US); Ip Hing Lai, Northern Territories (HK); Cheung Yik Man, Northern Territories (HK); Ho Wing Tak, Northern Territories (HK); Luk Ka Lok, Tuen Mun (HK); Chan Kim Ho, Tai Hang (HK); Mark Gerard Tebbe, Ventura, CA (US)

(73) Assignee: MUNCHKIN, INC., Van Nuys, CA (US)

( * ) Notice: Subject to any disclaimer, the term of this patent is extended or adjusted under 35 U.S.C. 154(b) by 0 days.

(21) Appl. No.: 17/213,124

(22) Filed: Mar. 25, 2021

(65) Prior Publication Data

US 2021/0283288 A1 Sep. 16, 2021

Related U.S. Application Data

(63) Continuation of application No. 17/198,072, filed on Mar. 10, 2021.

(Continued)

(51) Int. Cl.
*A61L 2/10* (2026.01)
*A61L 2/24* (2006.01)
(Continued)

(52) U.S. Cl.
CPC ..................................... *A61L 2/10* (2013.01)
; *A61L 2/24* (2013.01); *A61L 11/00* (2013.01);
*B65F 1/062* (2013.01);
(Continued)

(58) Field of Classification Search
CPC ..................................... A61L 2/10; A61L 2/24
See application file for complete search history.

(56) References Cited

U.S. PATENT DOCUMENTS 2,212,330 A 8/1940 Thomas
2,652,173 A 9/1953 Farrell
(Continued)

FOREIGN PATENT DOCUMENTS

CN 206108115 U 4/2017
CN 109516023 A 3/2019
(Continued)

OTHER PUBLICATIONS

Supplementary Partial European Search Report for EP/21768313, mailed Feb. 9, 2024. (15 pages).

(Continued)

*Primary Examiner* — Donald R Spamer
(74) *Attorney, Agent, or Firm* — Robert Z. Evora; ArentFox Schiff LLP

(57) ABSTRACT

A method of sterilizing a waste container with ultraviolet (UV) light is disclosed which includes, inserting an article of waste into the waste container, sealing the container from an external environment to prevent UV light from shining out, activating a UV sanitizing routine stored in a UV light module having at least one UV light source and irradiating an interior surface of the diaper pail with the UV light.

25 Claims, 23 Drawing Sheets

Related U.S. Application Data

(60) Provisional application No. 63/037,571, filed on Jun. 10, 2020, provisional application No. 63/028,212, filed on May 21, 2020, provisional application No. 62/987,683, filed on Mar. 10, 2020.

(51) Int. Cl.

| | |
|---|---|
| *A61L 11/00* | (2006.01) |
| *B65F 1/06* | (2006.01) |
| *B65F 1/16* | (2006.01) |
| *A61L 103/00* | (2026.01) |

(52) U.S. Cl.
CPC ................ *B65F 1/16* (2013.01); *B65F 1/163* (2013.01); *A61L 2103/23* (2026.01); *A61L 2202/122* (2013.01); *A61L 2202/14* (2013.01); *B65F 2210/129* (2013.01); *B65F 2210/168* (2013.01); *B65F 2240/132* (2013.01)

(56) References Cited

U.S. PATENT DOCUMENTS

| | | | |
|---|---|---|---|
| 3,831,514 | A | 8/1974 | Jernstrom |
| 4,349,123 | A | 9/1982 | Yang |
| 4,721,226 | A | 1/1988 | Yurko |
| 4,902,482 | A | 2/1990 | Faust |
| 5,115,935 | A | 5/1992 | Lemongelli |
| 5,337,581 | A | 8/1994 | Lott |
| D391,725 | S | 3/1998 | Triglia |
| D427,825 | S | 7/2000 | Mooney |
| 6,365,113 | B1 | 4/2002 | Roberts |
| 7,146,785 | B2 | 12/2006 | Stravitz |
| 7,617,660 | B2 | 11/2009 | Morand |
| 8,235,237 | B1 | 8/2012 | Stravitz |
| 8,484,936 | B2 | 7/2013 | Tannock |
| 2003/0121923 | A1 | 7/2003 | Morand et al. |
| 2004/0020175 | A1 | 2/2004 | Stravitz |
| 2006/0237461 | A1 | 10/2006 | Chomik et al. |
| 2008/0175751 | A1 | 7/2008 | Sun et al. |
| 2009/0100806 | A1 | 4/2009 | Morand |
| 2011/0017745 | A1 | 1/2011 | Michaels et al. |
| 2011/0100995 | A1 | 5/2011 | Dunn et al. |
| 2013/0233857 | A1 | 9/2013 | Yang et al. |
| 2015/0086420 | A1* | 3/2015 | Trapani ..................... A61L 9/20 |
| | | | 422/24 |
| 2015/0259140 | A1 | 9/2015 | Yang et al. |
| 2015/0324760 | A1* | 11/2015 | Borowski ............ B65F 1/0006 |
| | | | 705/308 |
| 2016/0167874 | A1 | 6/2016 | Dunn et al. |
| 2017/0291762 | A1 | 10/2017 | Wong |
| 2018/0110893 | A1* | 4/2018 | Chang ..................... B65F 1/062 |
| 2018/0155123 | A1* | 6/2018 | Parker ..................... B65F 1/068 |
| 2018/0194099 | A1 | 7/2018 | Wilcoxen et al. |
| 2018/0290828 | A1* | 10/2018 | Dunn ..................... B65F 1/163 |
| 2020/0039742 | A1 | 2/2020 | Chomik et al. |
| 2022/0044208 | A1 | 2/2022 | Borowski et al. |

FOREIGN PATENT DOCUMENTS

| | | | |
|---|---|---|---|
| KR | 10-2018-0083586 A | 7/2018 | |
| TW | M410729 U | 9/2011 | |
| TW | M561665 U | 6/2018 | |
| WO | 03/89312 A3 | 5/2004 | |
| WO | WO-2013134124 A1 * | 9/2013 | .............. B65F 1/062 |
| WO | 2020/056523 A1 | 3/2020 | |

OTHER PUBLICATIONS

Supplementary European Search Report on European Patent Application No. EP21816634, Jun. 21, 2024. (9 pages).

Amazon, "Kapoosh UV Sanitizing Waste Trash Can/Bin, Black," Available at: <https://www.amazon.in/Kapoosh-Sanitizing-Waste-Trash-Black/dp/B00BF8PM8Q>, Nov. 21, 2012, 4 pages.

International Preliminary Report on Patentability and Written Opinion received for PCT Patent Application No. PCT/US2021/035802, mailed on Dec. 15, 2022, 9 pages.

International Search Report and Written Opinion received for PCT Patent Application No. PCT/US2020/054864, mailed on Dec. 30, 2020, 8 pages.

International Search Report and Written Opinion received for PCT Patent Application No. PCT/US2021/035802, mailed on Aug. 25, 2021, 9 pages.

\* cited by examiner

METHOD OF STERILIZING WASTE CONTAINERS WITH ULTRAVIOLET LIGHT

CROSS REFERENCE TO RELATED APPLICATIONS

This Application is a Continuation of U.S. patent application Ser. No. 17/198,072 filed Mar. 10, 2021, which claims priority to U.S. Provisional Patent Application Ser. No. 62/987,683 filed Mar. 10, 2020, and to U.S. Provisional Patent Application Ser. No. 63/028,212 filed May 21, 2020; and to U.S. Provisional Patent Application Ser. No. 63/037,571 filed Jun. 10, 2020, the contents of all of which are hereby incorporated by reference herein in their entirety into this disclosure.

TECHNICAL FIELD

The subject disclosure relates generally to methods, systems and apparatuses configured to clean, disinfect, and/or sterilize a waste container with ultraviolet (UV) light. The UV light generated by the apparatus reduces or eliminates bacteria, viruses, malodor, pathogens and other potentially harmful microorganisms.

BACKGROUND

Most households possess at least one waste receptacle, while many households have multiple containers that hold or store waste therein. Diaper pails are specialized waste containers used by parents and other caregivers to temporarily store waste related to care of infants and young children. Dirty diapers are one of the most common articles of waste stored in diaper pails. Diapers, and waste more generally, often possess malodor and can exist in various states of decomposition, spoilage and decay. Waste can be a source of potentially harmful microorganisms such as bacterial, viruses, mold, fungus and other potentially harmful pathogens. Traditional waste receptacles thus present an environment for microorganisms to multiply, malodor to build and the process of decomposition to continue while the waste is stored therein.

Ultraviolet germicidal irradiation (UVGI) is the use of ultraviolet (UV) energy (electromagnetic radiation with a wavelength shorter than that of visible light) to kill or inactivate viral, bacterial, and fungal species. UV light also acts as a high energy catalyst that breaks down odor-causing volatile organic compounds (VOCs) into less complex molecules through a process called oxidation. When exposed to UV energy, VOC's are broken down into short lived oxygen and hydroxyl free radicals that in turn oxidize other complex molecules that may be present. The end result is an effective and immediate breakdown of odor causing molecules, with almost no chemical byproducts.

Thus, there is a need for a waste receptacle that harnesses the power of UV sterilization to clean the inside of the receptacle, reduce/eradicate potentially harmful microorganisms and reduce/eliminate VOCs that cause malodor.

SUMMARY OF THE SUBJECT DISCLOSURE

The present subject disclosure presents a simplified summary of the subject disclosure in order to provide a basic understanding of some aspects thereof. This summary is not an extensive overview of the various embodiments of the subject disclosure. It is intended to neither identify key or critical elements of the subject disclosure nor delineate any scope thereof. The sole purpose of the subject summary is to present some concepts in a simplified form as a prelude to the more detailed description that is presented hereinafter.

While various aspects, features, or advantages of the subject disclosure are illustrated in reference to common waste receptacles, such aspects and features also may be exploited in various other containers that may benefit from UV sterilization to improve cleanliness or eliminate potentially harmful microorganism and malodor.

To the accomplishment of the foregoing and related ends, the subject disclosure, then, comprises the features hereinafter fully described. The following description and the annexed drawings set forth in detail certain illustrative aspects of one or more embodiments of the disclosure. However, these aspects are indicative of but a few of the various ways in which the principles of the subject disclosure may be employed. Other aspects, advantages and novel features of the subject disclosure will become apparent from the following detailed description of various example embodiments of the subject disclosure when considered in conjunction with the drawings.

In an exemplary embodiment, the present subject disclosure is a waste receptacle. The waste receptacle includes a container housing, a lid assembly and at least one UV illumination source disposed in the lid assembly or container housing for sterilizing an internal compartment of the container housing. The waste receptacle may include at least one sensor, for example disposed in the lid assembly and/or the container housing, for ensuring the safe operation of the UV illumination source. The at least one sensor prevents the UV illumination source from operating unless the waste receptacle is completely sealed in order to prevent UV light from exiting the receptacle during use and to protect a user or bystander from exposure to potentially harmful UV light.

In another exemplary embodiment, the present subject disclosure is a method of sterilizing a waste receptacle with ultraviolet (UV) light, including the steps of: providing a container having a housing, a lid assembly and a support structure disposed between the housing and lid assembly; opening a cover lid of the lid assembly to deposit an article of waste into a waste chamber disposed in the support structure; closing the cover lid; engaging at least one sensor adapted to ensure that the cover lid is closed; and directing an ultraviolet (UV) light onto an interior surface of the diaper pail.

BRIEF DESCRIPTION OF THE DRAWINGS

Various exemplary embodiments of this disclosure will be described in detail, wherein like reference numerals refer to identical or similar components or steps, with reference to the following figures, wherein.

DETAILED DESCRIPTION

Figure 1:
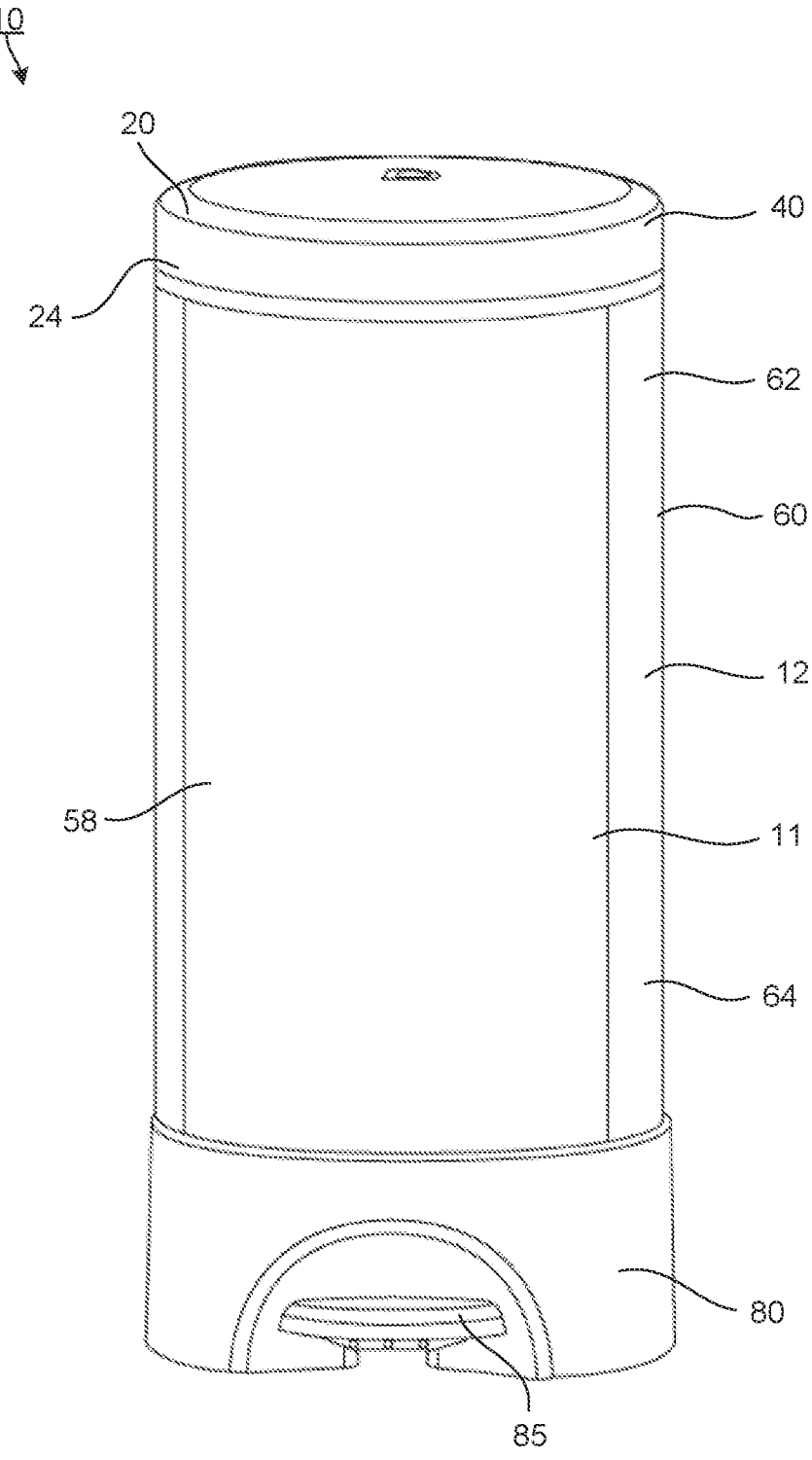
FIG. 1 is a front view of a UV sterilizing pail, according to an exemplary embodiment of the present subject disclosure.

Particular embodiments of ultraviolet (UV) light sterilizing waste containers, systems and methods will now be described in greater detail with reference to the figures.

The subject disclosure is described with reference to the drawings, wherein like reference numerals are used to refer to like elements throughout. In the following description, for purposes of explanation, numerous specific details are set forth in order to provide a thorough understanding of the present disclosure. It may be evident, however, that the present disclosure may be practiced without these specific details.

Various exemplary embodiments of the subject disclosure are presented throughout the figures. Multiple perspective views of a UV sterilizing pail 10 according to an exemplary embodiment of the present subject disclosure are presented in the figures. The components shown in the exemplary embodiment may be interchanged or substituted with an equivalent component without altering the scope of this subject disclosure. All such combinations are not shown for sake of brevity, but will be appreciated by one having ordinary skill in the art after consideration of the present subject disclosure.

Ultraviolet germicidal irradiation (UVGI) is the use of ultraviolet (UV) energy (electromagnetic radiation with a wavelength shorter than that of visible light) to kill or inactivate viral, bacterial, and fungal species. The UV spectrum is commonly divided into UV-A (wavelengths of 400 nm to 315 nm), UV-B (315 nm to 280 nm), and UV-C (280 nm to 100 nm). The entire UV spectrum from approximately 10 nm-400 nm is capable of being used according to this subject disclosure as it can kill or inactivate many microorganisms, however UV-C energy provides the most germicidal effect and destroys the DNA of microorganisms, including most antibiotic resistant bacteria.

Other benefits of the disclosed subject disclosure include eliminating foul odors. The UV light acts as an antibacterial by neutralizing germs that cause odor. The ultraviolet light also acts as a high energy catalyst, breaking down odor-causing volatile organic compounds (VOC's) into less complex molecules through a process called oxidation. The VOC's are broken down into short lived oxygen and hydroxyl free radicals that in turn oxidize other complex molecules that may be present. The end result is an effective and immediate breakdown of odor causing molecules, with almost no chemical byproducts. The UV light may kill up to 99.99% of problematic microorganisms including germs, fungus, viruses, bacteria, and the like.

FIG. 1 is a front view of a UV sterilizing pail 10 having a lid assembly 40 attached at an upper end 62 of a housing 60 and a base 80 having a foot pedal 85 attached at a lower end 64 of the housing 60. The UV sterilizing 10 pail has a front side 11 and a rear side 13 (FIGS. 5-6), and a door 8 disposed on the front side 11 for accessing an interior storage space 58 disposed inside the housing 60. A support structure or support member 70 is adapted to hold various flexible bag assemblies 100 that extend into the interior storage space 58 of the pail 10 for the storage of waste. A UV sterilizing module 50 having at least one UV light source 51 (FIG. 15) is disposed inside the lid assembly 40 for sterilizing interior surfaces 29 of the pail 10 and the contents stored therein.

Figure 2:
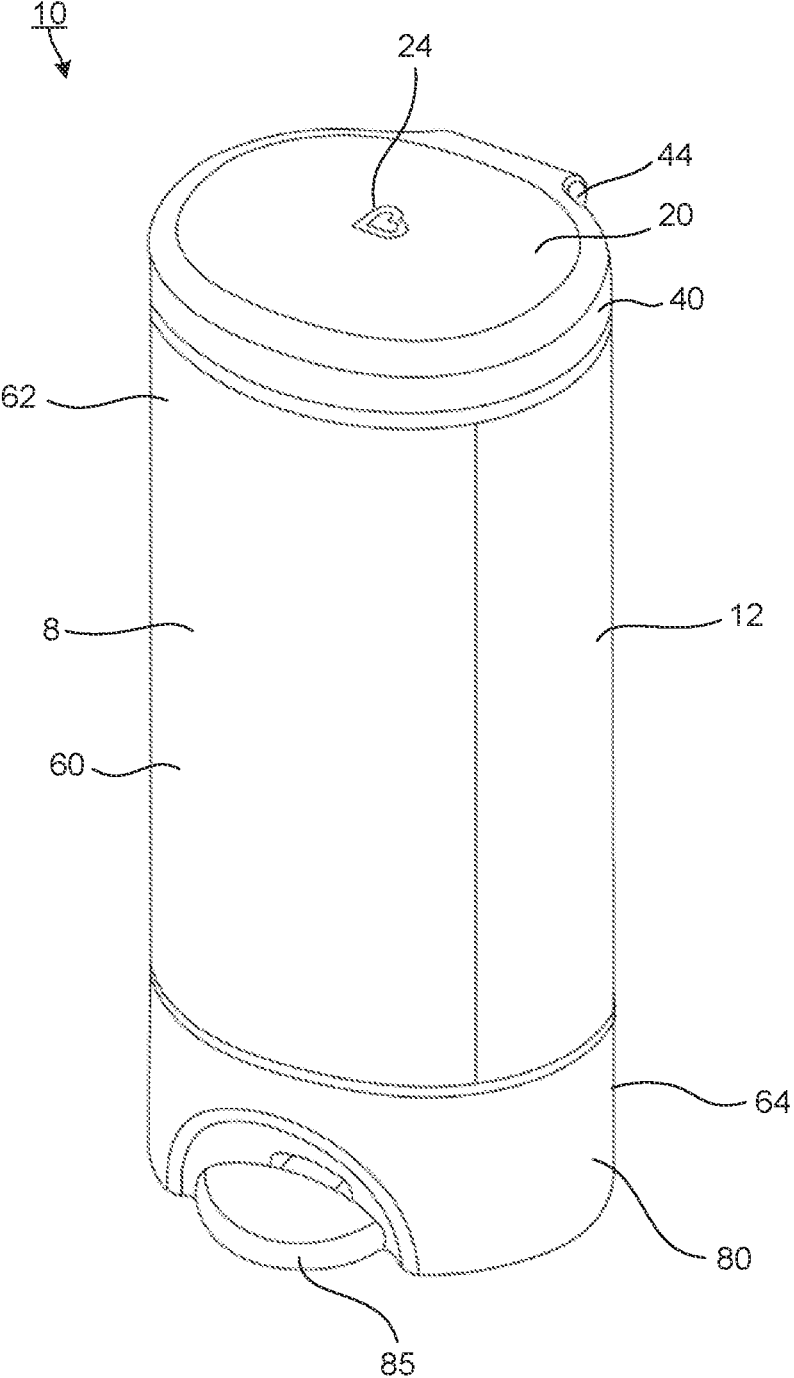
FIG. 2 is a front perspective view of the UV sterilizing pail, according to an exemplary embodiment of the present subject disclosure.

FIG. 2 illustrates a front perspective of the UV sterilizing pail 10. The UV sterilizing pail 10 may have at least one exterior surface 12. The external surfaces 12 define the outer limits of the UV sterilizing pail 10 and include the outside walls of the housing 60, the base 80, and lid assembly 40. The lid assembly 40 may be attached to the support structure 70 or the housing 60 by a hinge 44.

As shown in FIG. 2, the UV sterilizing pail 10 is shown as being substantially cylindrical, but it is not limited to such a shape and may be any shape as long as it functions as described herein. For example, the UV sterilizing pail 10 may be shaped as a three-dimensional solid that is cubic, cuboid, conic, spherical, pyramidal, substantially a triangular prism, substantially a rectangular prism, substantially a pentagonal prism, substantially a hexagonal prism, substantially a prism having a heart shaped cross-section, substantially a prism having a cross-section shaped like an animal or character, and the like, according to this subject disclosure. The lid assembly 40, housing 60, support structure 70 and base 80, and the components found therein, may be comprised of thermoplastic, thermosets, various elastane materials, silicone, metal and metal alloys, ceramics, wood, natural fibers and/or any other suitable material according to this subject disclosure.

Figure 3:
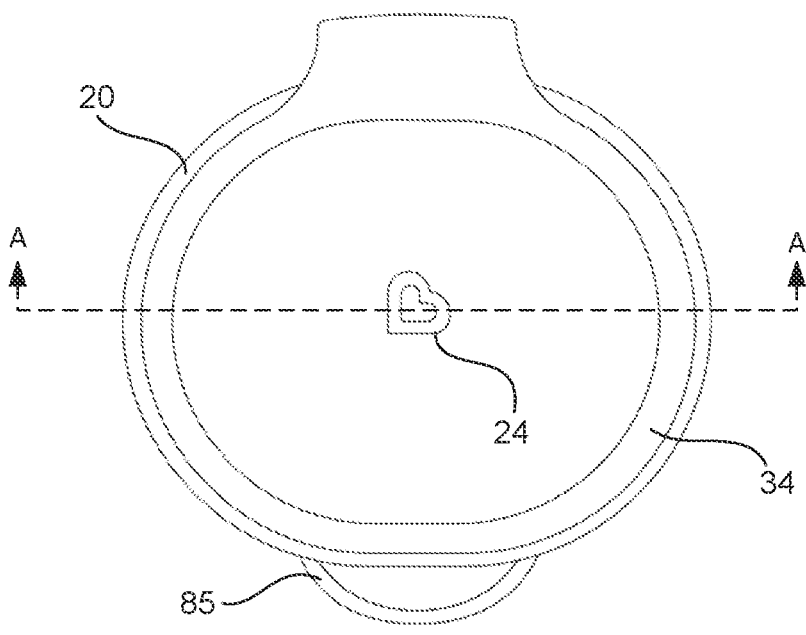
FIG. 3 is a top view of the UV sterilizing pail, according to an exemplary embodiment of the present subject disclosure.
Figure 4:
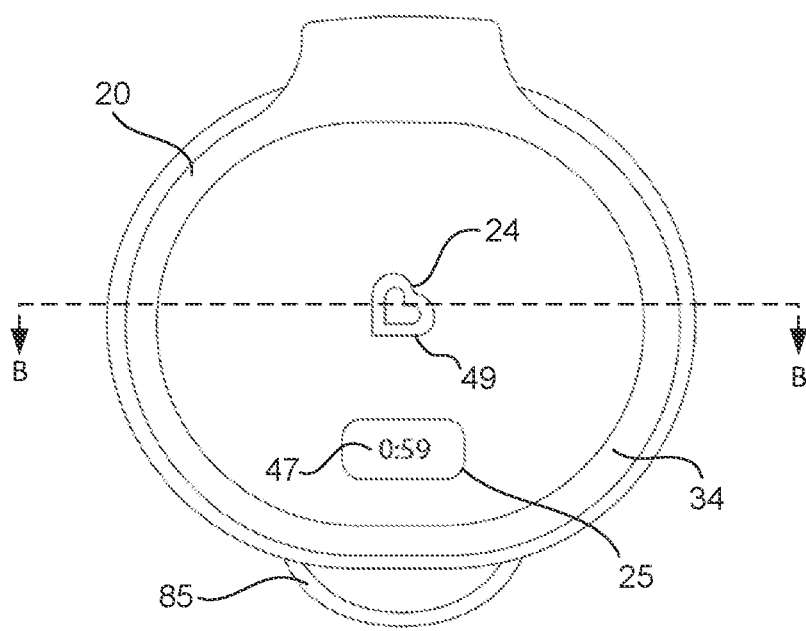
FIG. 4 is a top view of the UV sterilizing pail, according to an exemplary embodiment of the present subject disclosure.
Figure 9:
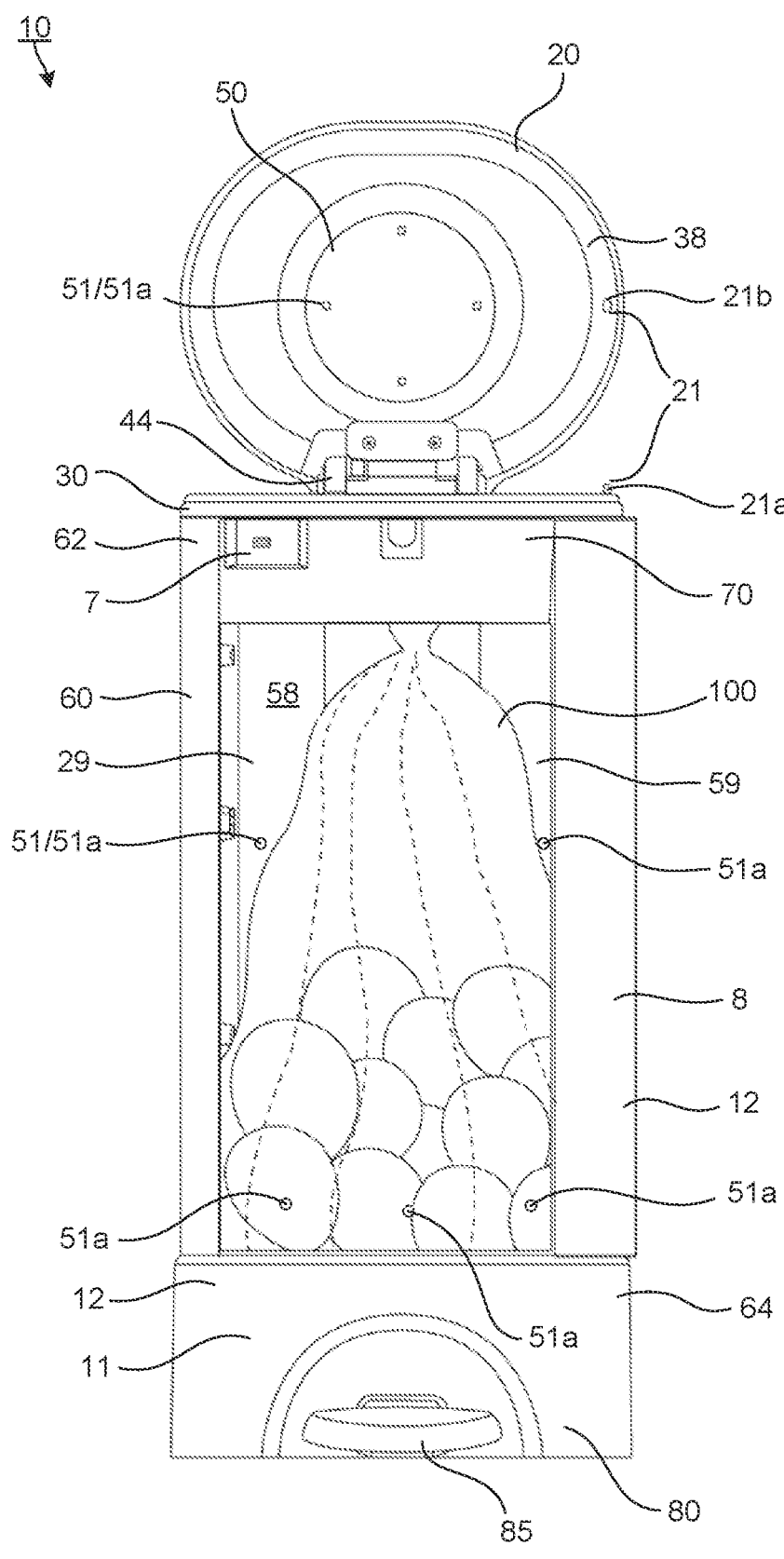
FIG. 9 is a front view of the UV sterilizing pail with the lid cover and a housing door shown in an open position with a flexible bag installed therein, according to an exemplary embodiment of the present subject disclosure.

FIGS. 3-4 show the lid cover 20 has an external surface 34 that may include an operating light 24. The operating light 24 is presented in a heart shape throughout the specification and drawings, but it is not limited to such a shape and may be any shape as long as it functions as described herein. The operating light 24 is shown as being disposed on the lid cover 20, but the operating light 24, or additional operating indicators may be located on any surface of the UV sterilizing pail 10. The operating light 24 serves as an indicator that indicates the status of a UV sterilizing routine 5 (FIG. 16) performed by the UV sterilizing module 50 (FIG. 9). The operating light 24, for example, may blink during the duration of the UV sterilizing routine 5. This indicates to a user or bystander that the UV sterilizing module 50 is active and that the UV light 51 is on and transmitting UV irradiation. When the UV sterilizing routine 5 is finished, the operating light 24 may stop blinking and return to a solid steady color, thereby indicating to a user or bystander that the UV light sources 51 in the UV sterilizing pail 10 are off.

Alternatively, the operating light 24 may change colors to indicate that the UV sterilizing routine 5 is running. An "off" state may be indicated by, for example, a red light, while an "on" state may be indicated by a blue light. Any color combination may be used to indicate the operation of the UV sterilizing module 50 and status of the UV sterilizing routine 5 according to this subject disclosure. Furthermore, the operating light may flash or cycle through various colors in order to communicate status information about the UV sterilizing routines 5. Any number of color schemes or light pulsing patterns can be configured to indicate use or non-use during the operation of the UV sterilizing pail 10. Various safety features are incorporated into the UV sterilizing pail 10 to ensure that the UV sterilizing routine 5 immediately terminates when the pail 10 is opened, and will be described in greater detail below.

As shown in FIG. 4, the UV sterilizing pail may include a control interface 25 for controlling a control module 52

(FIG. 15A) of the UV sterilizing module 50. The control interface 25 is shown as being disposed on the lid cover 20 but may be disposed on any surface of the UV sterilizing pail 10 or accessory. The UV control interface 25 may be mechanical and include physical buttons, switches, and actuators, or as shown in FIG. 4, the control interface 25 may be a touchscreen. The control interface 25 is one way to input commands into the control module 52. The control interface 25 may be used to dictate the time length of the UV sterilizing routine 5. The control interface 25 may include a power switch 49 for switching the UV sterilizing module 50 from the "on" state to the "off" state. The control interface 25 may include a timer 47 for indicating the time remaining in a cleaning cycle of the UV sterilizing routine 5. Additionally, either the control interface 25 or the UV sterilizing module 50 may include a communication transceiver 46 for remotely operating the UV sterilizing pail 10 from an appropriate device, such as a phone, computer, remote control, and the like. The communication transceiver 46 may be any form of wireless technology, including, but not limited to, a radio transceiver 46, a Bluetooth adapter, modem, mobile broadband modem, and/or the like according to this subject disclosure.

Figure 5:
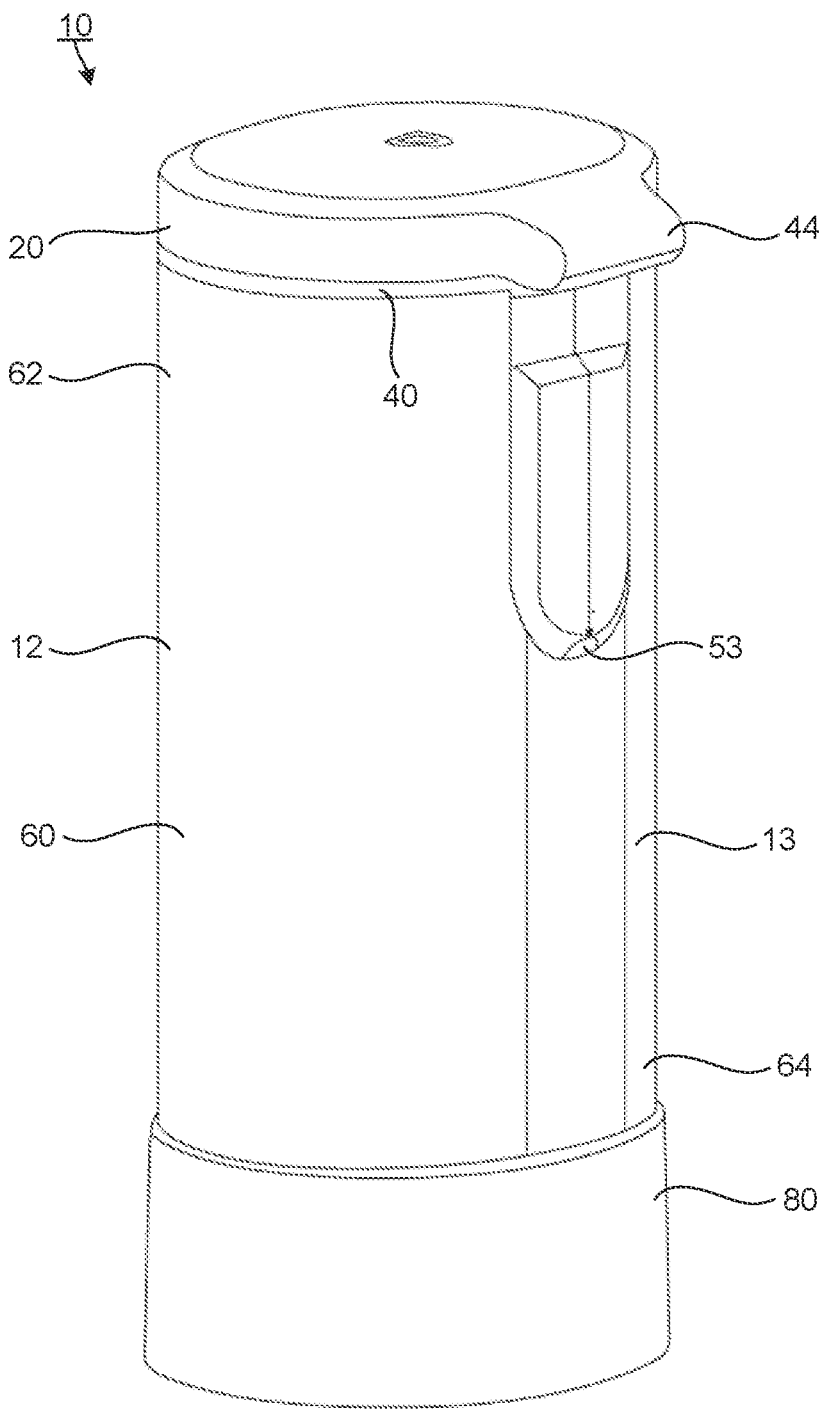
FIG. 5 is a rear perspective view of the UV sterilizing pail, according to an exemplary embodiment of the present subject disclosure.
Figure 6:
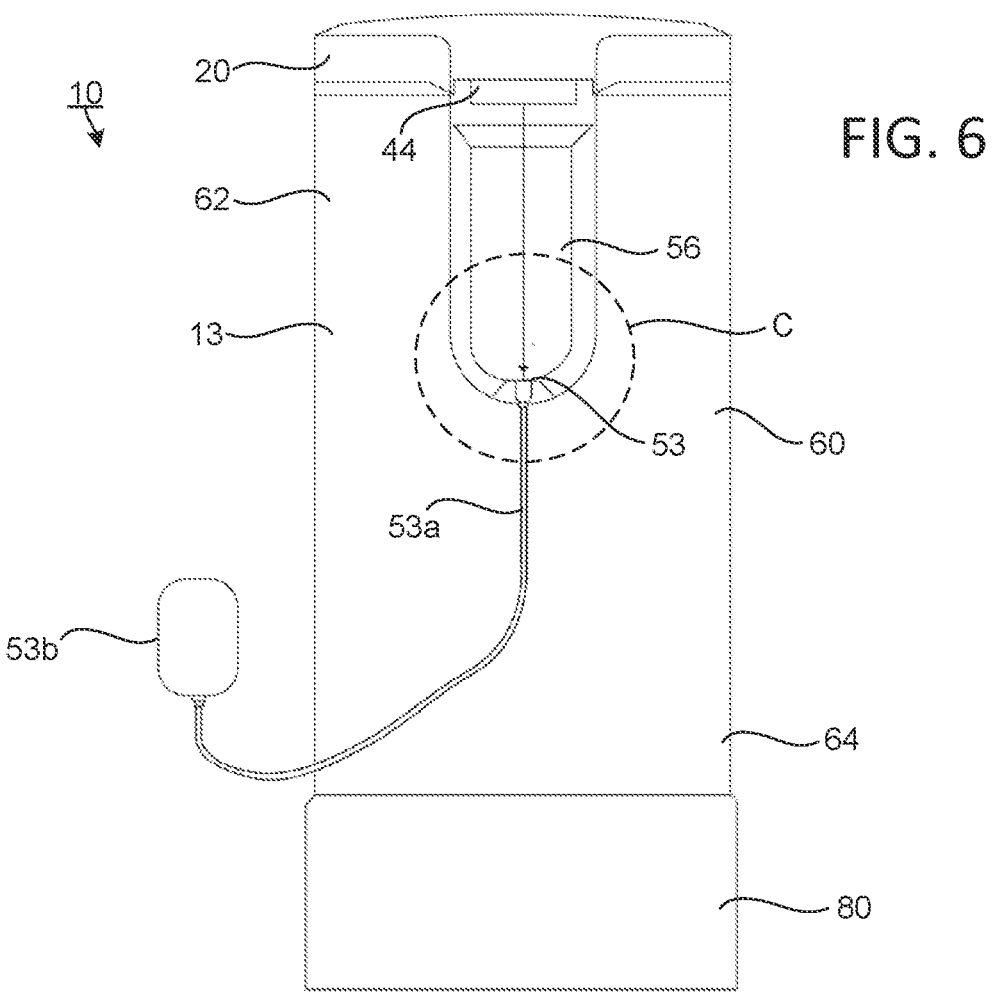
FIG. 6 is a rear view of the UV sterilizing pail with a wall plug and an adapter installed therein, according to an exemplary embodiment of the present subject disclosure.
Figure 7:
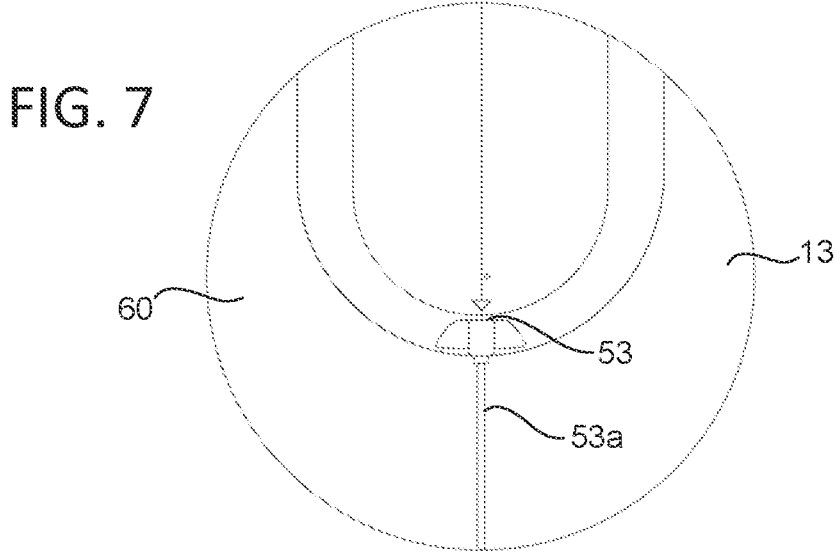
FIG. 7 is a close up view of section "C" highlighted in FIG. 6 showing the adapter installed in the UV sterilizing pail, according to an exemplary embodiment of the present subject disclosure.

FIG. 5 is a rear perspective view of the UV sterilizing pail 10. The hinge 44 may be disposed on the rear side 13 of the UV sterilizing pail 10 and connect the lid cover 20 to the lid assembly 40. A power source outlet 53 may be disposed on the rear side 13 of the pail 10. As shown in further detail in FIGS. 6-7, the power source outlet 53 may interface with an adapter 53a that fits therein on one end, and connects to a plug 53b on the other end for attachment to a wall socket to provide electricity and power to the UV sterilizing pail 10. The UV sterilizing pail 10 may be configured to include a battery to hold a charge and power in reserve when the pail 10 is not plugged into an outside power source, or the pail 10 may be configured as a direct coupled power system directly connected to a dc load in order to power the pail 10 without storing energy or an excess charge therein. The battery may be replaceable or rechargeable and configured with a USB port, or similar, to enable charging of the battery. The UV sterilizing module 50 may also be powered through solar power generated by a solar panel (not shown) that may be disposed on the UV sterilizing pail 10. The power source outlet 53 is shown as being disposed on the rear side 13 of the housing 60, but may be disposed on any surface of the UV sterilizing pail 10.

Figure 8:
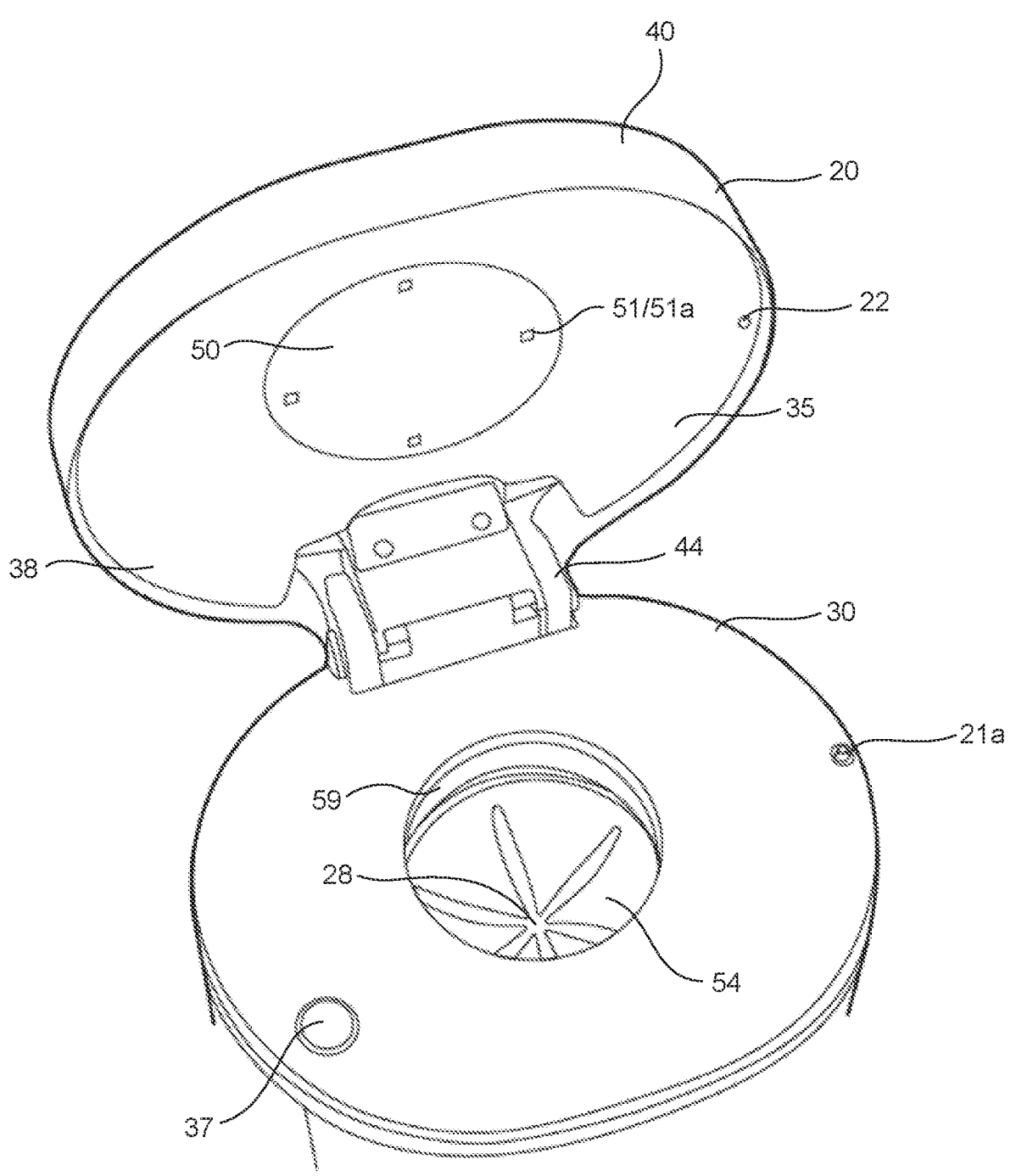
FIG. 8 is a top perspective view of the UV sterilizing pail with a lid cover shown in an open position, according to an exemplary embodiment of the present subject disclosure.

FIG. 8 is a top perspective view of the UV sterilizing pail 10 with the lid cover 20 in an open position. The lid assembly 40 may include the cover lid 20 and an internal lid 30. Alternatively, the lid assembly 40 may only include the lid cover 20 connected by the hinge 44 to the housing 60 or support structure 70. A waste chamber 59 (FIGS. 11-13) is disposed in the support structure 70. The waste chamber 59 is adapted to receive and secure flexible bag assemblies 100, such as cassettes 101 for dispensing pleated tubing, and single use flexible bags 110. The internal lid 30 opens and closes over the waste chamber 59 and helps to secure and captivate the flexible bag assemblies 100 in place. When the internal lid 30 is closed over the cassette 101, a slight compressive force is provided by the internal lid 30 to prevent flexible tubing 106 of the cassette 101 (FIG. 17) from being drawn outward from within the cassette 101 when waste is inserted into the UV sterilizing pail 10. Instead, when waste is inserted into the UV sterilizing pail 10, the internal lid 30 controls the direction in which the flexible tubing 106 is extended, such that the flexible tubing 106 feeds into the opening 28 disposed in the waste chamber 59 that leads into the interior storage space 58. Further, when the internal lid 30 is closed, an internal downward projection lip 33 (FIG. 11) on the internal lid 30 serves to press down and essentially lock the cassette 101 in position to a degree such that a corresponding interior upper portion of the cassette 101 receives the downward compression force of the downward projection lip 33. This secures the cassette 101 in place and presses down on the flexible tubing 106 with enough force as to prevent the downward movement of the flexible tubing 106 each time further waste is disposed within the UV sterilizing pail 10. Upon release of the internal lid 30, the flexible tubing 106 may be pulled out and cut by bag cutter 61 to tie and dispose of the used flexible tubing 106, as needed. The flexible tubing 106 is then pulled down further to tie a knot and start a subsequent bag.

Referring back to FIG. 8, the hinge 44 attaches the lid cover 20 and the internal lid 30 to the support structure 70 and the housing 60 in order to facilitate the opening and closing of both lids 20, 30. A rotatable sealing gripping mechanism 54 is provided in the waste chamber 59. The rotatable sealing gripping mechanism 54 has a resilient opening 28 in a flexible material that is provided through which the flexible bags assemblies 100 or flexible tubing 106 may pass through the opening 28 therein. The rotatable sealing gripping mechanism 54 is constructed and arranged to create a restricted portion within the flexible bag assemblies 100 to provide a temporary odor seal. This is accomplished by gripping and twisting the flexible bag assemblies 100 to provide a temporary seal, as will be described in greater detail below.

A lid latch button 37 may be disposed on the support structure 70 and extend through the internal lid 30 for opening the door 8. Once the door 8 is open, the user may interact with a lid latching mechanism 36 (FIGS. 11-12) in order to open the internal lid 30. The lid latching mechanism 36 is described in further detail as FIG. 4 in U.S. Pat. No. 8,833,592 (the '592 patent), which is incorporated by reference herein in its entirety into this disclosure. For the sake of brevity, the details of the physical description of the lid latching mechanism 36 will not be repeated again here.

As shown in FIG. 8, the UV sterilizing module 50 may be disposed in a lid cover housing 35 located in the lid cover 20. The UV sterilizing module 50 may extend through a bottom surface 38 of the lid cover housing 35. The bottom surface 38 of the lid cover housing 35 may be substantially flat, convex or concave. The bottom surface 38, or any surface of the UV sterilizing pail 10 may be composed of a reflective material. The bottom surface 38, or any surface of the UV sterilizing pail 10 may be contoured at a predetermined angle to encourage reflectivity of the UV light. At least one UV light source 51 may be disposed on the UV sterilizing module 50. The UV light source 51 may be a UV LED light 51a adapted to generate UV-C light having a radiation range with wavelength between 100-280 nm, with a peak range between 275-280 nm. The UV light source 51 may generate UV-A light between 315-400 nm and UV-B light between 280-315 nm. The UV light source 51 may generate visible light between 380-700 nm with a peak wavelength between 395-405 nm. The UV light source 51 may be adapted to generate one or more type of light simultaneously in order to maximize the sterilization process.

The UV LED lights 51a may have a forward voltage between 6-7.5 V, an optical power output between 5-6 mW and radiant flux of approximately 256 uw/cm^2. A second UV LED 51a of the UV light source 51 may have a forward voltage between 3.1-3.4 V and an optical power output between 20-50 mW. A converter may be provided with the UV light module 50 for controlling the radiation intensity of the UV light source 51.

As shown in FIG. 8, there are four UV LED lights 51a arranged on the UV sterilizing module. The UV LED lights 51a may be arranged as four points located in a square pattern on the UV sterilizing module 50. However, it is to be understood that the number of UV light sources 51 and the configuration of the UV light sources 51 on the sterilizing module 50 is not limited to such a number or pattern and may be arranged in any number, configuration or pattern as long as it functions as described herein.

FIG. 9 is a front view of the UV sterilizing pail 10 with the lid cover 20 and the door 8 shown in an open position and a flexible bag assembly 100 installed therein. The flexible bag assembly 100 and contents of its bag are shown as partially see-through in order to show the UV LED lights 51a disposed on the interior surfaces 29 of the housing 60 behind the bag assembly 100. A more detailed description of the configuration of UV light sources in the housing 60 and lid assembly 40 will be discussed below.

Figure 10:
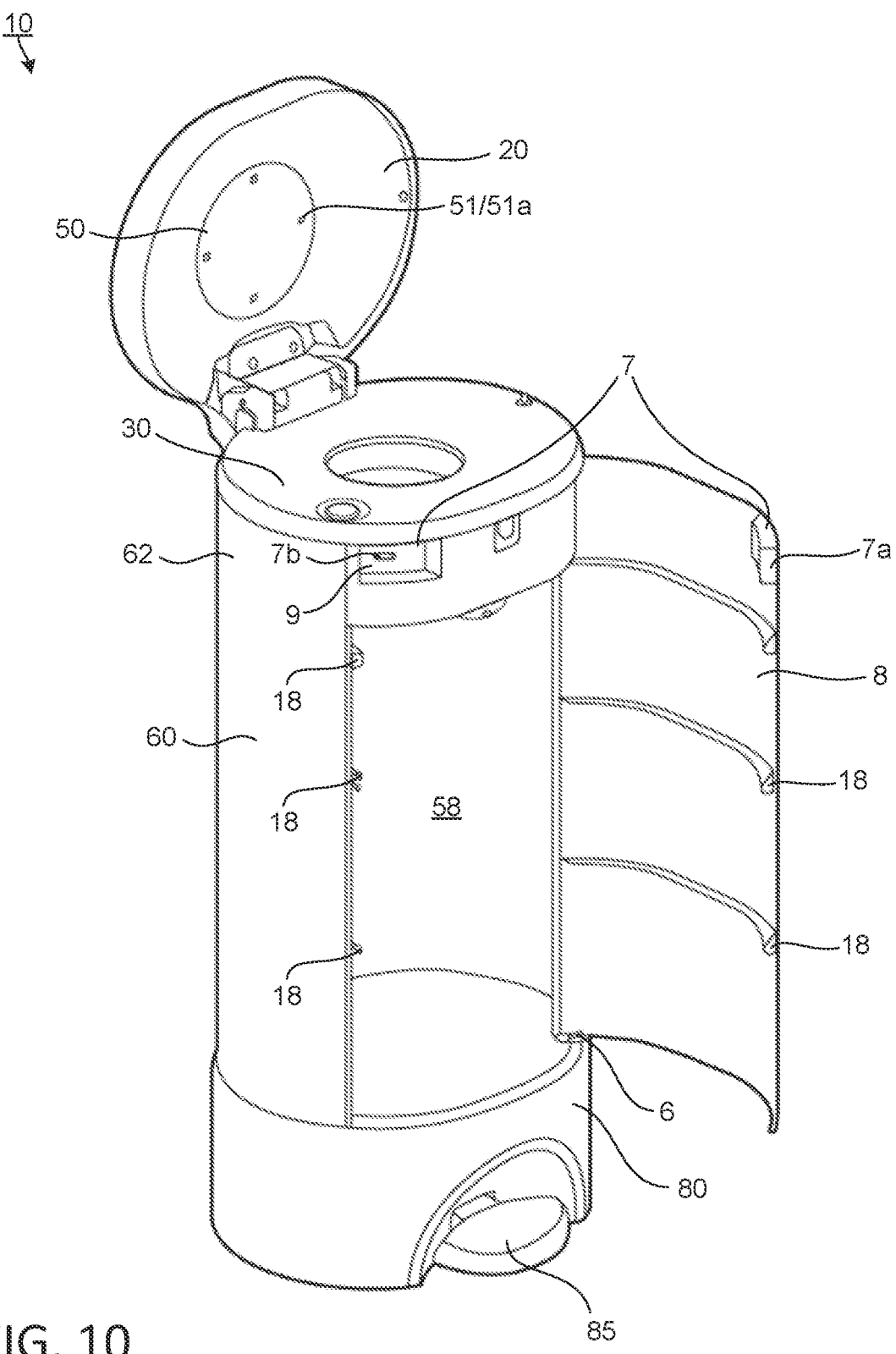
FIG. 10 is a front perspective view of the UV sterilizing pail with the lid cover and housing door shown in an open position, according to an exemplary embodiment of the present subject disclosure.
Figure 11:
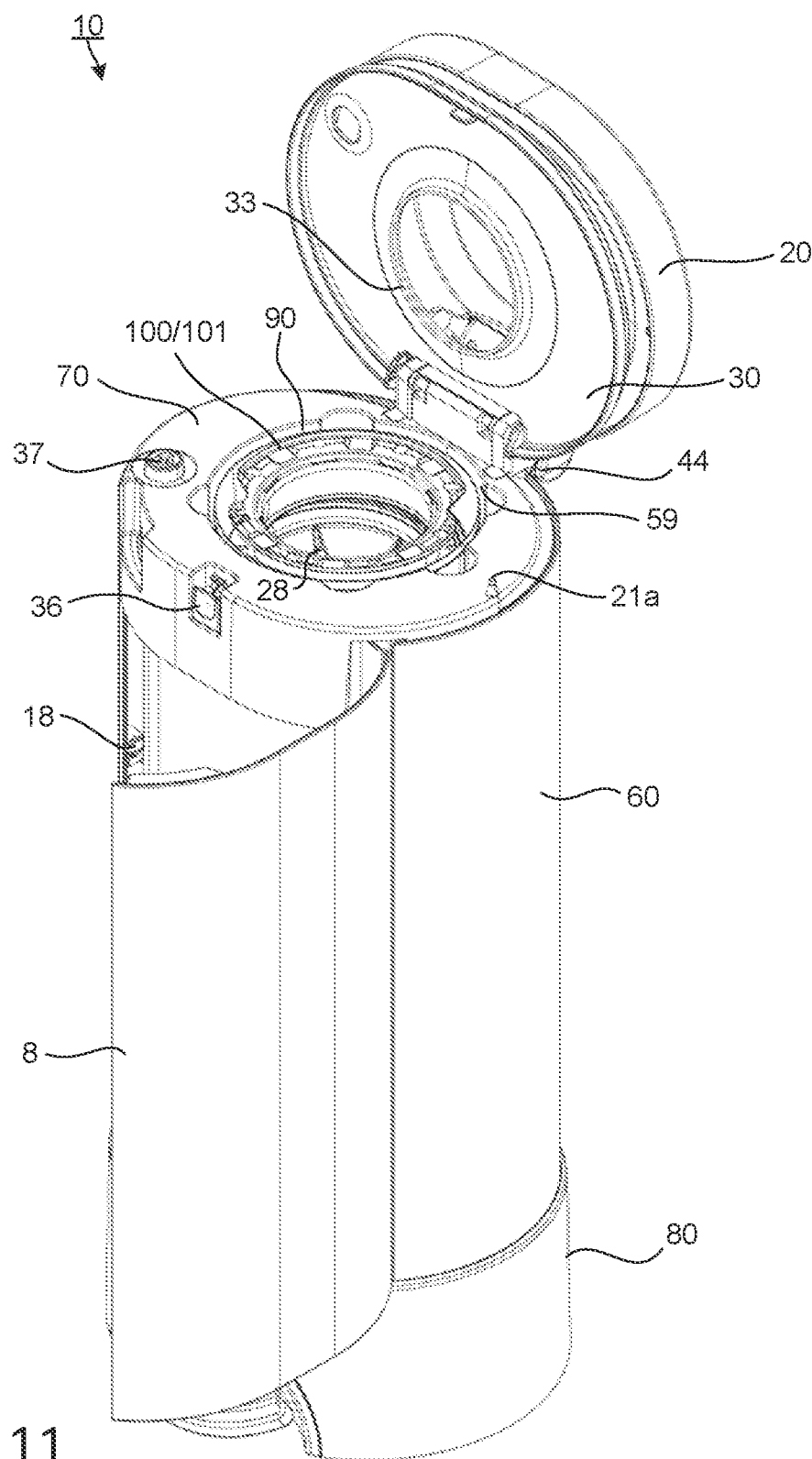
FIG. 11 is a front perspective view of the UV sterilizing pail with the lid cover and an internal lid shown in an open position with a cassette installed in a support structure, according to an exemplary embodiment of the present subject disclosure.
Figure 13:
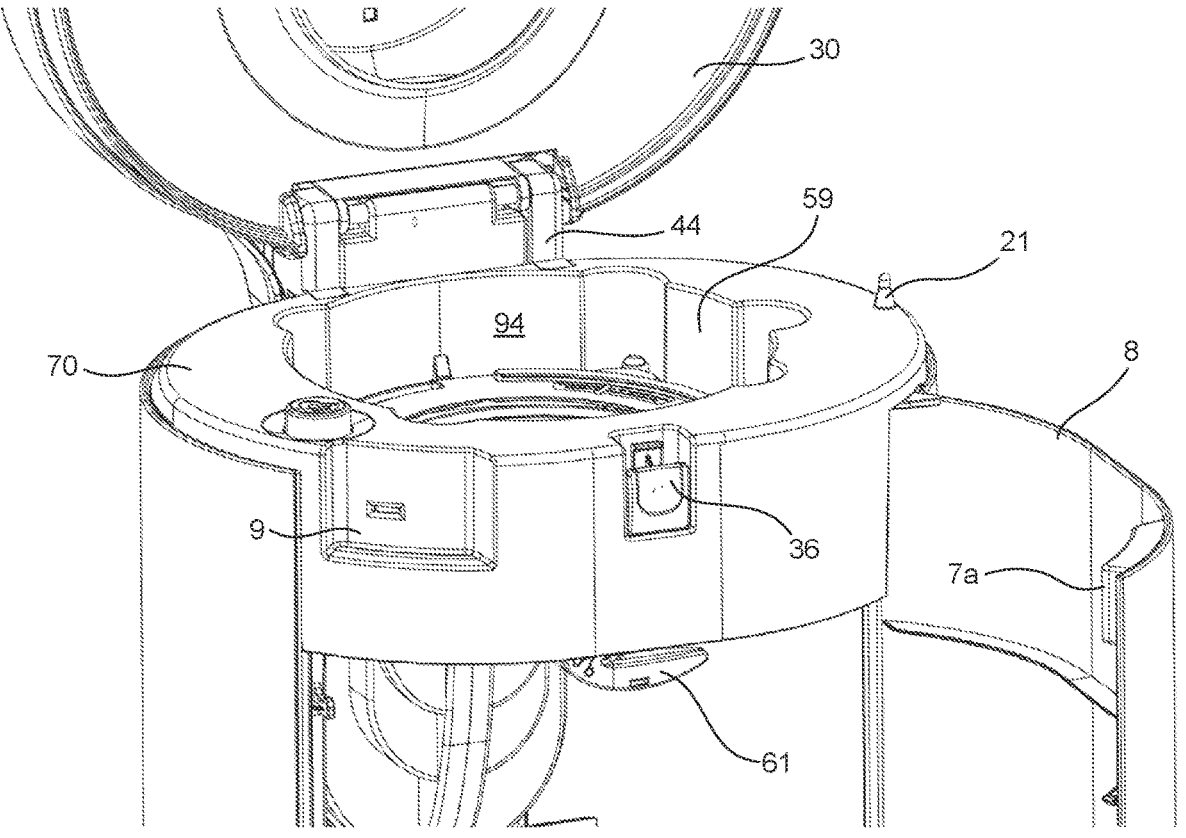
FIG. 13 is a close-up front perspective view of the UV sterilizing pail with the lid cover, internal lid and housing door shown in an open position, according to an exemplary embodiment of the present subject disclosure.
Figure 14:
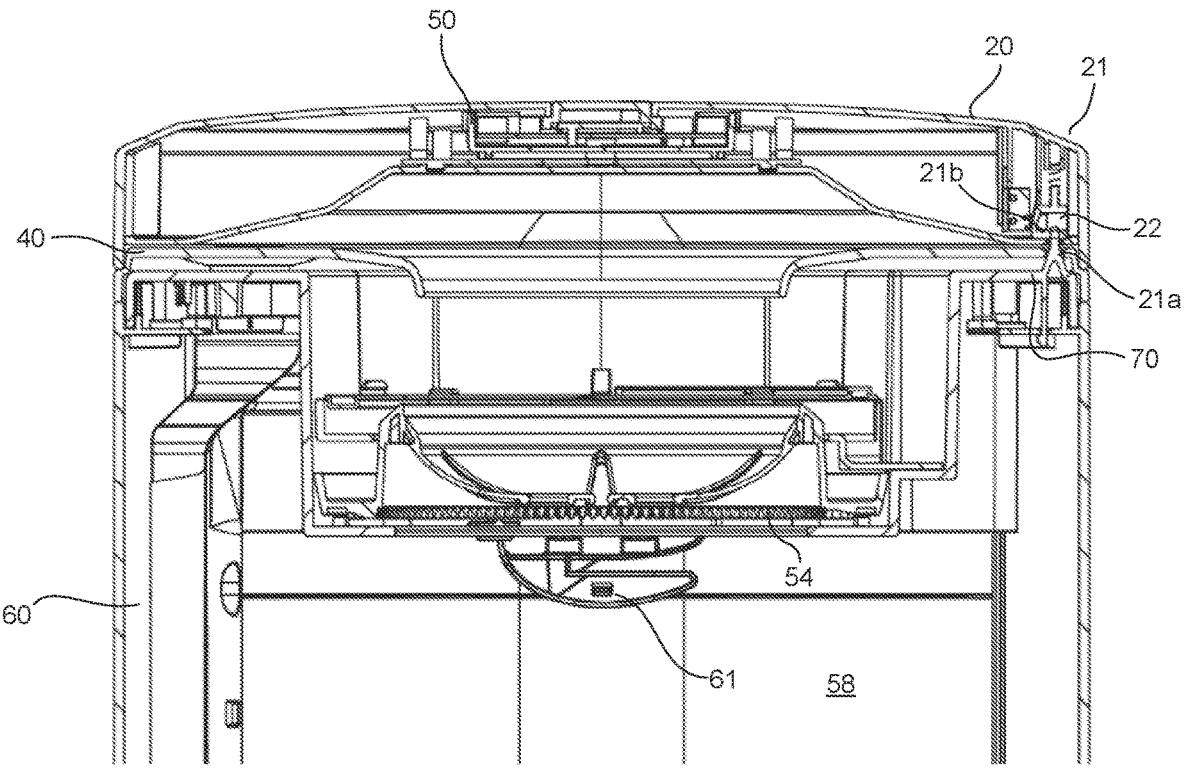
FIG. 14 is a cross section of the UV sterilizing pail along plane A-A of FIG. 3 through a lid sensor assembly, according to an exemplary embodiment of the present subject disclosure.

FIGS. 9-11 show both elements (21a, 21b) of a lid sensor assembly 21 (see also FIGS. 13-14). The lid sensor assembly 21 may be a mechanical sensor comprising an actuator post 21a disposed on the support structure 70, and a trigger 21b that may be spring-loaded disposed in a sensor recess 22 on the lid cover 20. The actuator post 21a may extend through the internal lid 30 in order to contact the sensor recess 22 on the lid cover 20. Alternatively, the actuator post 21a may be disposed directly on the internal lid 30. When the lid cover 20 is shut against the support structure 70, the actuator post 21a contacts and moves the trigger 21b past a threshold that causes the completion of an electric circuit 55 that provides power to the UV sterilizing module 50. If the lid sensor assembly 21 is not engaged, then the UV sterilizing module 50 will not be able to operate. Alternatively, the lid sensor assembly 21 may be a magnetic proximity sensor such as a hall switch, a reed sensor, or another proximity sensor such as a photoelectric sensor, optical sensor, inductive sensor, capacitive sensor, and/or the like according to this subject disclosure.

FIG. 10 shows both elements (7a, 7b) of a door sensor assembly 7. An actuator button 7b is disposed in a button recess 9 on the upper portion 62 of the housing 60. The actuator button 7b is actuated by a door post 7a that is disposed on the door 8 of the UV sterilizing pail 10 (See also FIG. 13). When the door 8 is shut against the housing 60, it latches shut by way of a door latch 18. At the same time, the door post 7a actuates the actuator button 7b past a threshold that causes the completion of the electric circuit 55 that provides power to the UV sterilizing module 50. If the door 8 is not completely closed against the housing 60, then the door sensor assembly 7 is not engaged and the UV sterilizing module 50 will not be able to operate. Alternatively, the door sensor assembly 7 may be a magnetic proximity sensor such as a hall switch, a reed sensor, or another proximity sensor such as a photoelectric sensor, optical sensor, inductive sensor, capacitive sensor, and/or the like according to this subject disclosure.

Exposure to UV light may damage a viewer's eyes or skin. It is therefore of crucial importance that the light generated by the UV sterilizing module 50 be contained within the UV sterilizing pail 10 in a secure and safe manner. To this end, the UV sterilizing pail 10 will not operate unless both the lid cover 20 and the door 8 are closed, and both the lid sensor assembly 21 and the door sensor assembly 7 are engaged.

The UV sterilizing pail 10 may have additional safety sensors or features in order to ensure the safe operation of the UV sterilizing module 50. For example, the UV sterilizing pail 10 may have reinforced seams or overlapping seams so that UV light may not escape from within the pail 10. Additionally, the lid cover 20 or the UV sterilizing module 50 may include at least one accelerometer 41. The accelerometer 41 may be a multi-axis sensor that measures the acceleration due to gravity in more than one direction. A tri-axis accelerometer 41 may be used to detect the position of the UV sterilizing module 50 in three dimensions so that the UV sterilizing module 50 may be configured to only operate in certain resting positions. For example, the UV sterilizing module 50 may be configured to only operate when the lid cover 20 is resting substantially parallel to the surface supporting the UV sterilizing pail 10. This would correspond to the lid cover 20 being in a closed position such that the UV light is safely contained within the UV sterilizing pail 10. Alternatively, the accelerometer 41 in the UV sterilizing module 50 or lid cover 20 may recognize when the lid cover 20 is open because the UV sterilizing module 50 would be substantially orthogonal (or any degree other than approximately orthogonal) to the horizon, and consequently the UV sterilizing module 50 would not activate.

The UV sterilizing pail 10 may include at least one proximity sensor (not shown) that may activate at least one motor (not shown) disposed in the lid assembly 40, hinge 44, support structure 70, housing 60 or base 80 in order to open the lid cover 20. The motor may also be adapted to engage a transmission mechanism 56 (discussed below) in order to drive the rotatable sealing and gripping mechanism 54 open or closed upon reception or absence of a stimulus by the proximity sensor, More than one proximity sensor may be disposed on the UV sterilizing pail 10 in order to create an overlapping field having a threshold that must be met before the lid cover 20 will open.

As shown in FIG. 10, the interior storage space 58 is accessible from a front side 11 of the UV sterilizing pail 10 through the door 8 attached to the housing 60 by at least one door hinge 6. The door 8 may be positioned at any location on the UV sterilizing pail 10 for accessing the interior storage space 58. Alternatively, the housing 60 may not include the door 8. The door latch 18 enables the door 8 to securely close against the housing 60. An undercut or recess (not shown) may be defined in the housing 60 on an opposite side of housing 60 at the upper end 62 from the hinge 44 in order to give the consumer space to be able to exert lifting pressure on a lifting surface of the lid cover 20.

Figure 12:
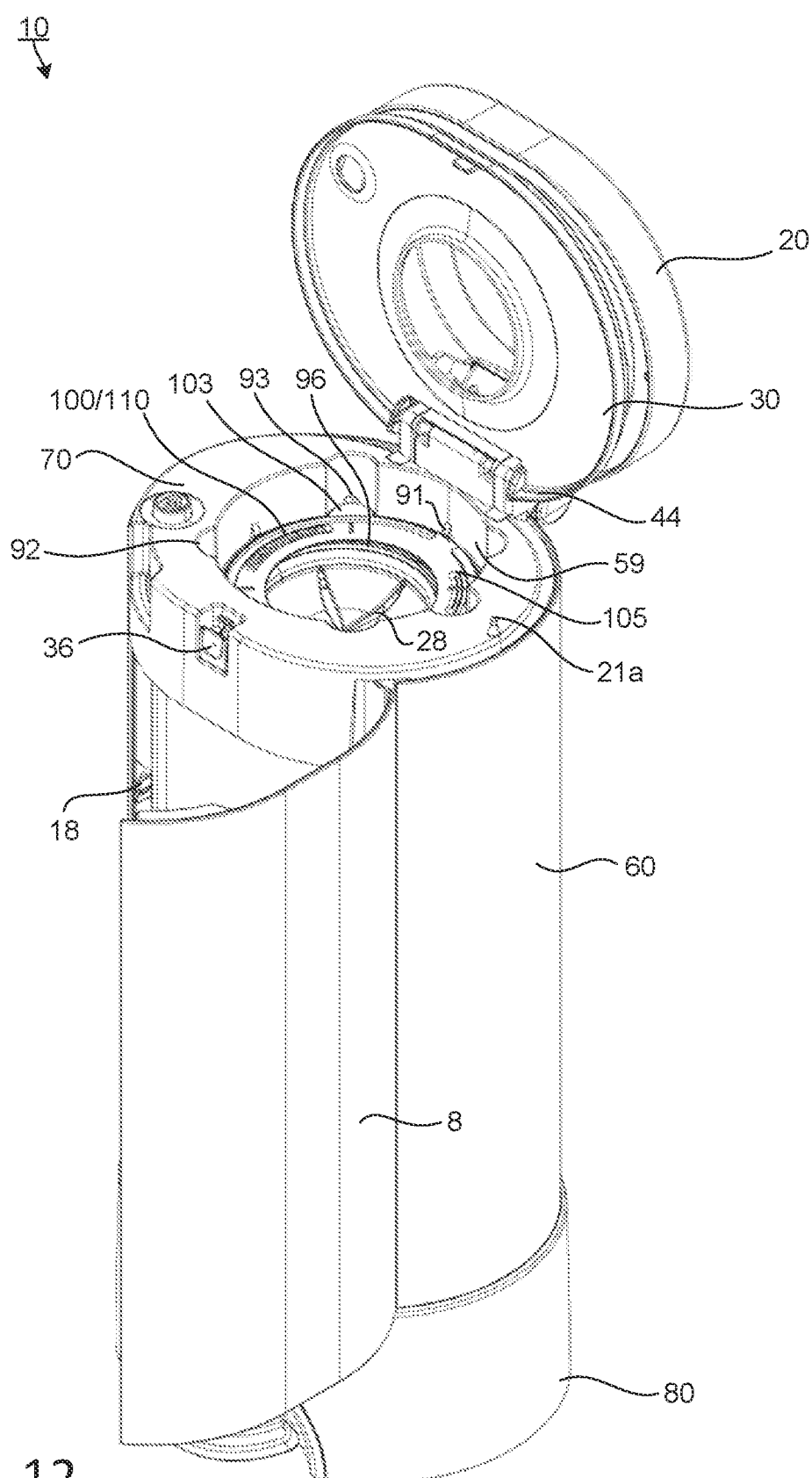
FIG. 12 is a front perspective view of the UV sterilizing pail with the lid cover and internal lid shown in an open position with a single use flexible bag installed in a support structure, according to an exemplary embodiment of the present subject disclosure.

FIGS. 11-12 show front perspective views of the UV sterilizing pail 10 with the cover lid 20, interior lid 30 and door 8 shown in an open position. In FIG. 11, the cassette 101 for dispensing pleated tubing is installed in the waste chamber 59 of the UV sterilizing pail 10. In FIG. 12, the single use flexible bag 110 having a frame 105 is installed in the waste chamber 59. Exemplary embodiments of cassettes for dispensing pleated tubing are described in U.S. Pat. Nos. 10,435,235 and 10,913,626, which are incorporated by reference herein in their entirety into this disclosure. An exemplary embodiment of the single use flexible bag 110 is described in U.S. Pat. No. 9,714,138, which is incorporated by reference herein in its entirety into this disclosure. For the sake of brevity, the details of the physical construction of the cassette 101 body and the single use flexible bag 110 and frame 105 will not be repeated again here.

As shown in FIGS. 11-13, the UV sterilizing pail 10 may be adapted for use with various styles of flexible bag assemblies 100 and may include a cylindrical recess 94 and a circular bottom receiving plate 96 having a first support structure or support member 90 and a second support structure or support member 91 for accommodating the flexible bag assemblies 100. The first support structure 90 may be adapted to hold and secure the single use flexible bag 110. The first support structure 90 may include recesses 92 having a semi-circular shape for receiving external tabs 103 of the frame 105 of the single use flexible bag 110 and securing these tabs 103 in place by use of a tab clip 93. The second support structure 91 may be adapted to hold and secure the cassette 101 and may include key projections that project upward a predetermined distance so that they mate with complementary apertures at a bottom portion of the cassette 101. The key projections may be adapted to control the position or the rotation of the cassette 101. Exemplary flexible bag support structures are described in U.S. Pat. No. 10,906,737 (the '737 patent), which is incorporated by reference herein in its entirety into this disclosure. For the sake of brevity, the details of the physical descriptions of the first support structure 90 and the second support structure 91 will not be repeated again here.

FIG. 14 is a cross section of the UV sterilizing pail 10 along plane A-A of FIG. 3 through the lid sensor assembly 21. The UV sterilizing pail 10 may include the bag cutter 61 (FIG. 13) for cutting the flexible tubing 106 in order to dispose of a full section of tubing 106 and retie off a fresh knot 102 to begin a new section for further use. The lid sensor assembly 21 is shown as a mechanical sensor comprising the actuator post 21a disposed on the support structure 70 and the trigger 21b that may be spring-loaded disposed in the sensor recess 22 on the lid cover 20. When the lid cover 20 is shut against the support structure 70, the actuator post 21a contacts and moves the trigger 21b past a threshold that causes the completion of an electric circuit that provides power to the UV sterilizing module 50. If the lid sensor assembly 21 is not engaged, then the UV sterilizing module 50 will not be able to operate.

Figure 15:
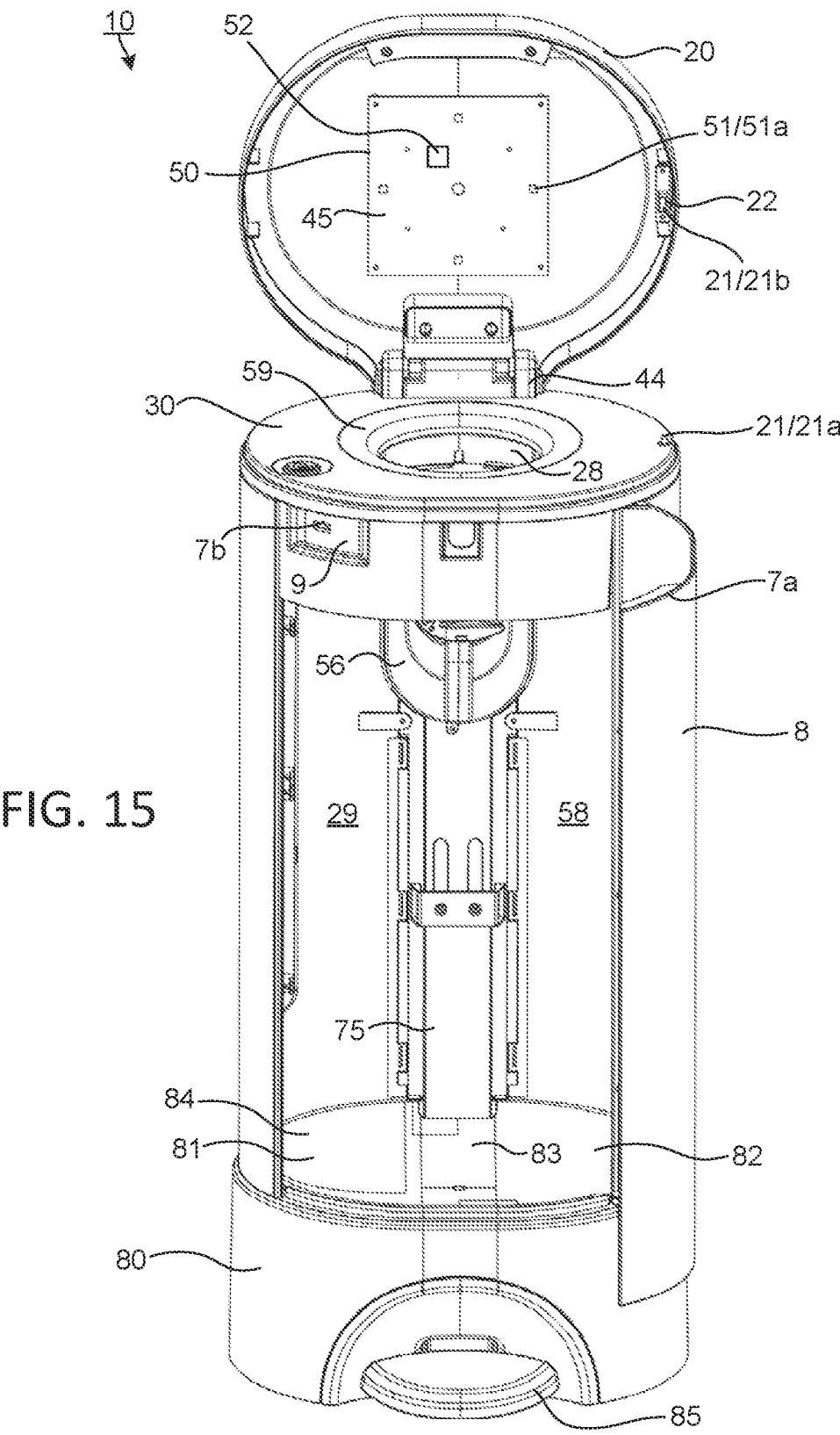
FIG. 15 is a front view of the UV sterilizing pail with the lid cover and housing door shown in an open position and with a lid cover housing removed, according to an exemplary embodiment of the present subject disclosure.

FIG. 15 is a front perspective view of the UV sterilizing pail 10 with the door 8 open and the lid cover 20 shown in an open position with the lid cover housing 35 removed. A substrate 45 of the UV sterilizing module 50 is shown with four UV LEDs 51a embedded into the substrate 45.

Figure 15A:
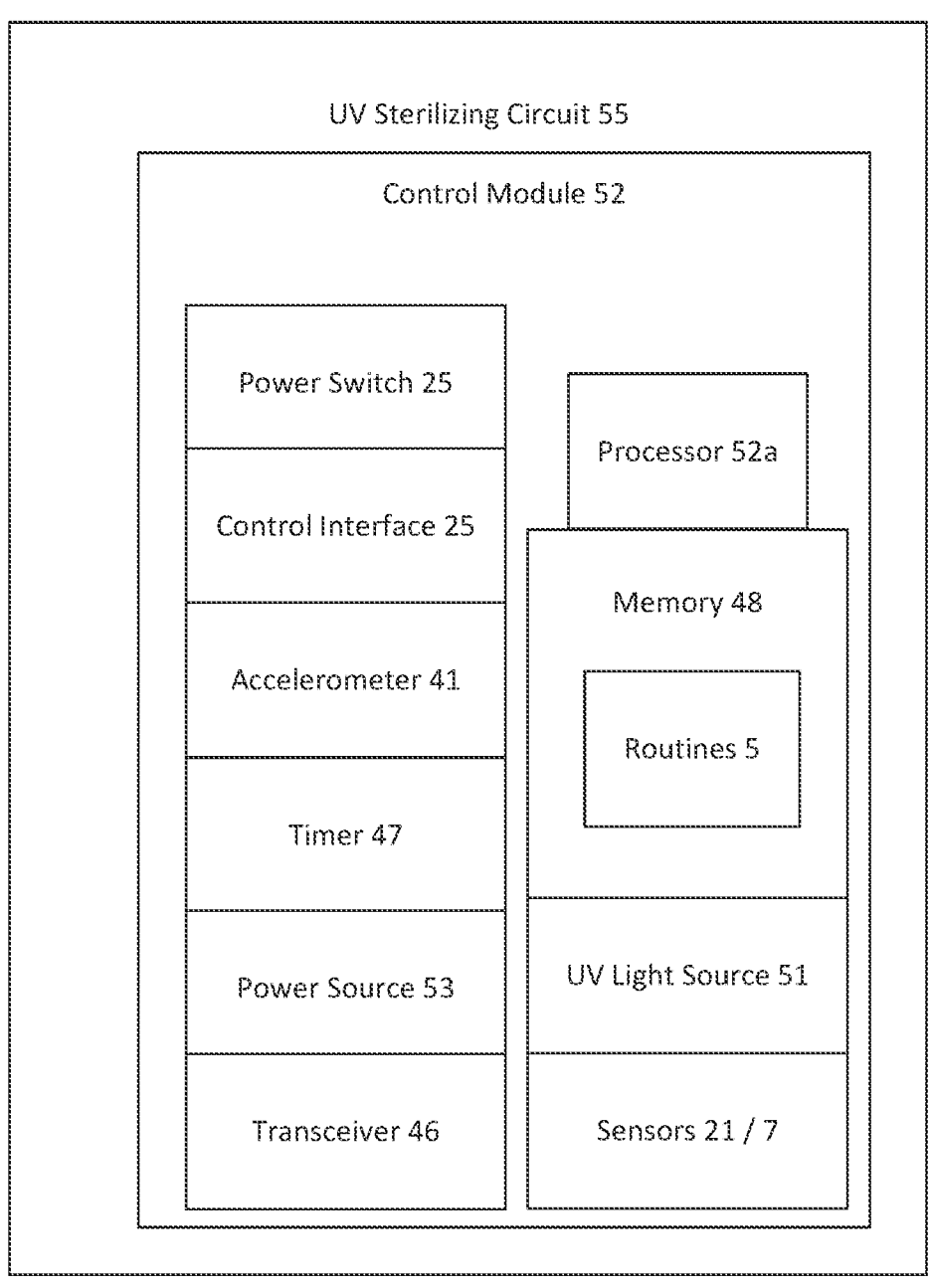
FIG. 15A is a diagram of a UV sterilizing circuit, according to an exemplary embodiment of the present subject disclosure.

FIG. 15A shows a diagram view of an exemplary UV sterilizing module 50. The UV sterilizing module 50 may consist of various components in a circuit 55, such as a control module 52 having a processor 52a, memory 48 having embedded UV sterilizing routines 5, a power source 53, a door sensor assembly 7 and a lid sensor assembly 21, a communication transceiver 46, control interface 25, accelerometer 41, timer 47, power switch 49, and at least one UV light source 51. The UV light sources 51 may be UV light emitting diodes (LEDs) 51a, as shown, or may be any other suitable light source capable of generating UV light for sterilizing the UV Sterilizing pail 10.

The communication transceiver 46 may be a radio transceiver, in order to receive and transmit information or commands from a mobile device, remote control, or other wireless device. The timer 47 may be embedded within the processor 52a. Various types of memory 48 may be embedded within the UV sterilizing module 50. Various sterilization routines 5 may be stored within the memory 48 and may be carried out by the processor 52a to operate the UV sterilizing module 50. The memory 48 may be adapted to store data related to the use of the UV sterilizing pail 10. The data acquired and stored may be shared with a remote server or other cloud application in order to generate a user profile or helpful tips or advice for the user. The duration of the sterilization routine 5, intensity of the UV light, activation pattern of the UV light sources 51, and other operational variables may be dictated by the control module 52. A USB port or other port may be provided for power charging or data transmission. The sterilizing routines 5 substantiated in the memory 48 of the UV sterilizing module 50 may be updated periodically by over the air data downloads or by way of the USB port. These components may be integrated substantially into a single unit disposed in the lid cover housing 35, or may be integrated into the lid assembly 40, the housing 60, the support structure 70, the base 80, or other UV sterilizing pail accessories.

The components of the UV sterilizing module 50 may also be contained in a modular detachable housing, such as a UV sterilizing puck 2 or the like, that may be removably attached to the UV sterilizing pail 10. By embedding the UV sterilizing module 50 and circuitry in a modular manner, the UV sterilizing module 50 can be adapted for use with a variety of containers not limited to waste containers where UVGI sterilization is desired by a user. An exemplary embodiment of a UV sterilizing puck 2 will be discussed in greater detail below.

Figure 15B:
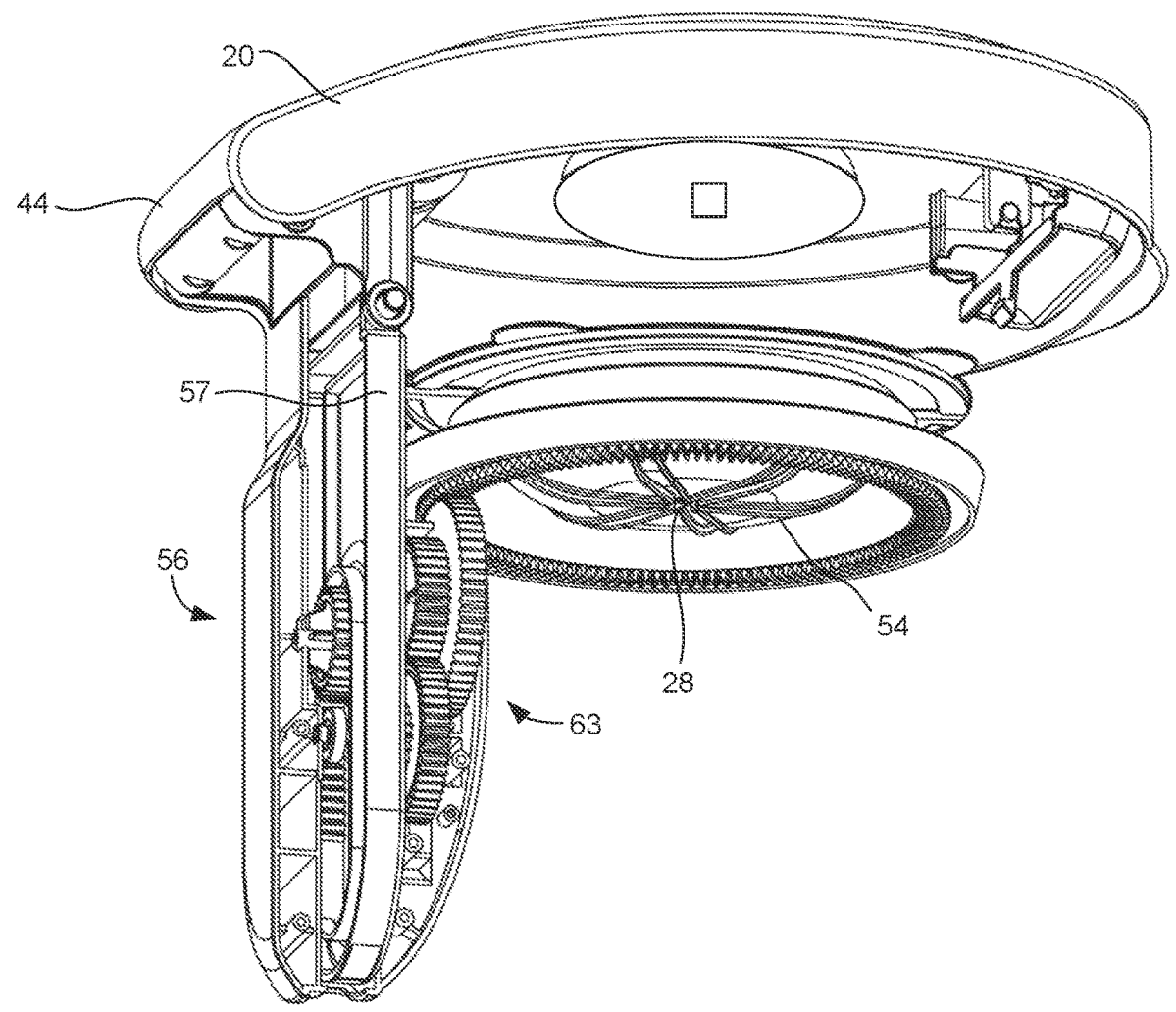
FIG. 15B is a side perspective view of a transmission mechanism, according to an exemplary embodiment of the present subject disclosure.

FIGS. 15 and 15B shows portions of the transmission mechanism 56 and related components. As shown in FIGS. 11-14, the waste chamber 59 contains the rotatable sealing and gripping mechanism 54 having a resilient opening 28 that flexible bag assemblies 100 are fed through. The transmission mechanism 56 is adapted to rotate the rotatable sealing and gripping mechanism 54 in order to twist a portion of the flexible bag assembly 100 to seal the passage of the flexible bag assembly 100 closed, thereby creating a temporary odor seal. The transmission mechanism 56 causes rotation of the rotatable sealing and gripping mechanism 54 when the lid cover 20 is moved from an open position to a closed position and is designed so as not to cause any movement of the rotatable sealing member 54 when the lid cover 20 is pivoted upwardly from the closed position to the open position.

As shown in FIG. 15B, the transmission mechanism 56 includes a push rod member 57 that is caused and constrained to slide linearly downwardly when the lid cover 20 is closed and linearly upwardly when it is opened. When the lid cover 20 is pivoted downwardly by a user from the open position to the closed position, the push rod member 57 will be driven downwardly and the rotatable sealing gripping mechanism 54 will be driven by a gear train mechanism 63 to rotate for a predetermined angular distance, thereby creating a twisted portion in the flexible bag assembly 100. The transmission mechanism 56 and the rotatable sealing gripping mechanism 54 are described further in the '737 patent, the entirety of which is incorporated by reference into this disclosure. The transmission mechanism 56 is also described in further detail as FIG. 12 in the '592 patent, which is incorporated by reference herein in its entirety into this disclosure. For the sake of brevity, further details of the physical descriptions of the rotatable sealing gripping mechanism 54 and the transmission mechanism 56 will not be repeated again here.

FIG. 15 shows elements of a foot pedal connection mechanism 75 that is in communication between the foot pedal 85 and the lid cover 20 in order to open the lid cover 20 when the foot pedal 85 is depressed. Alternatively, the UV sterilizing pail 10 may not include the foot pedal. The foot pedal 85 is described further in the '737 patent, the entirety of which is incorporated by reference into this disclosure. The foot pedal is also described further in U.S. Pat. No. 2,910,206, which is incorporated by reference herein in its entirety into this disclosure. For the sake of brevity, further details of the physical descriptions of the foot pedal 85 and its operation will not be repeated again here.

FIG. 15 also shows further detail of the base 80 of the UV sterilizing pail 10. The base 80 includes a receiving structure 81 for aligning and centering a flexible bag assembly 100 within the interior storage space 58 of the housing 60. The receiving structure 81 includes a bottom surface 82 defining a lowermost extent of the interior storage space 58 that includes a central flat portion 83 and an annular curved portion 84 surrounding the central flat portion 83. The receiving structure 81 is adapted to receive the flexible bag assembly 100 when it is full of waste. This configuration enhances the overall balance and stability of the UV sterilizing pail 10 in use.

Figure 16:
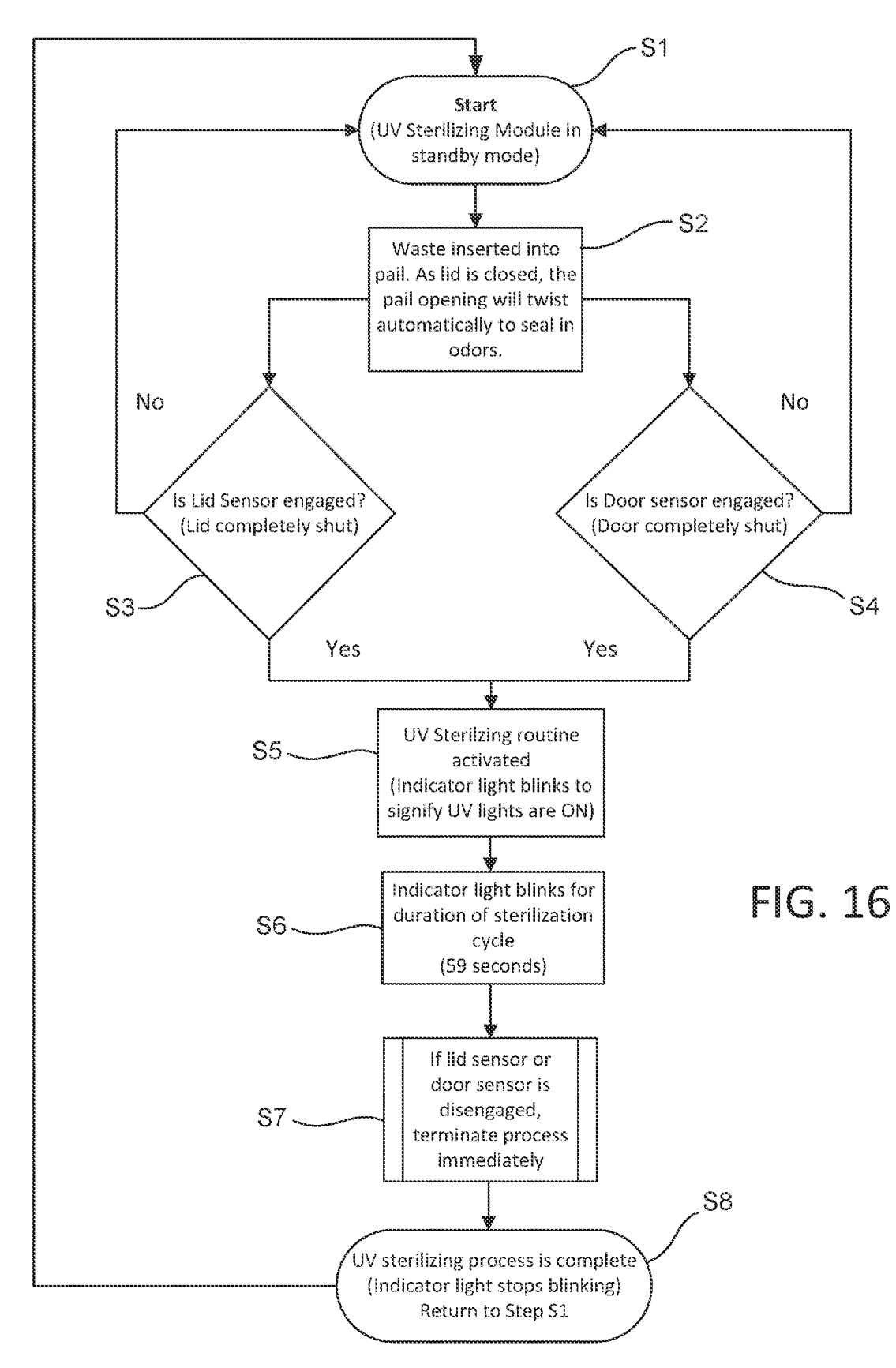
FIG. 16 is flow chart diagraming the operation of a UV sterilizing module with safety sensors, according to an exemplary embodiment of the present subject disclosure.

FIG. 16 shows a flow diagram of an exemplary UV sterilizing routine 5 carried out by the UV sterilizing module 50. Before step S1, a user opens the lid cover 20 and the internal lid 30 and installs a flexible bag assembly 100 therein, pushing the bag 100 past the rotatable sealing and gripping mechanism 54 through the opening 28 and into the interior storage space 58 disposed in the housing 60. Then, the user connects the plug adapter 53a, 53b into the UV sterilizing pail 10 at the adapter end 53a and into a wall socket with the plug 53b. Step S1, "Standby mode" begins when the operating light 24 comes on as an indicator that the UV sterilizing pail 10 has power and is available for sterilization. The UV sterilizing pail 10 is now ready for use.

In step S2, the user inserts an item of waste into the flexible bag assembly 100 and closes the lid cover 20 completely. The rotatable sealing and gripping mechanism 54 will automatically twist the flexible bag assembly 100 in order to seal in odors. Once the lid cover 20 is closed completely and the door 8 is tightly shut against the housing 60, steps S3 and S4 will occur in which the UV control module 52 verifies that both the lid sensor assembly 21 and door sensor assembly 7 are engaged. If the lid sensor assembly 21 and the door sensor assembly 7 are engaged, then the circuit 55 providing power to the UV sterilization module 50 will be complete, and the UV sterilization routine 5 may begin. If either the lid sensor assembly 21, or the door sensor assembly 7 is not engaged, then the control module 52 returns to step S1, with the UV light module 50 in "standby" mode.

The UV sterilizing module 50 may be adapted to automatically begin the UV sterilizing routine 5 when the lid cover 20 is shut and both the lid sensor assembly 21 and the door sensor assembly 7 are engaged. Alternatively, a user may input a command to begin the sterilization routine 5 by way of the control interface 25. For the safety of the user and potential bystanders, the UV sterilization module 50 will not have power or the ability to operate unless the lid sensor assembly 21 and the door sensor assembly 7 are engaged with both the lid cover 20 and the door 8 completely shut.

When the sterilization routine 5 begins sterilizing in step S5, the operating light 24 will blink to signify that UV sterilization is in progress. As discussed above, different protocol or systems may be substantiated between the UV sterilization module 50 and the operating light 24 in order to signify the current state of the UV sterilizing pail 10 to the user. For example, different colors displayed by the operating light 24 may signifying an "on" state and an "off" state.

In step S6, the operating light will continue to blink for the duration of the sterilization routine 5. In an exemplary embodiment of a sterilization routine 5, UV sterilization may last for 59 seconds, but it is not limited to such a duration and may be any duration, shorter or longer, as long as it functions as described herein.

Step S7 is a subroutine that is continuously running when the UV sterilization module 50 is in operation. If at any time during the operation of the UV sterilization module 50 the lid sensor assembly 21 or door sensor assembly 7 is disengaged because either the lid cover 20 or door 8 is opened, then the sterilization routine will terminate immediately and the UV sterilization module 50 will return to step S1 "standby" mode. If the UV sterilization routine 5 is interrupted or terminated for any reason, the UV sterilizing process will reset and begin from step S1.

In step S7, when the sterilization routine 5 is complete, the operating light 24 will stop blinking and the user will be able to open the lid cover 20, internal lid 30, or door 8 freely. The control module 52 then returns back to Step S1 and remains in standby mode until further use.

The UV light generated in the UV sterilization routine 5 may be a continuous exposure or may be intermittent bursts or pulses of UV light that expose the inner surfaces of the UV sterilizing pail 10 to UV light. Different sterilization routines 5 may be programed into the memory to be performed by the processor of the control module 52 of the UV sterilizing module 50. For example, the UV sterilizing module 50 may be adapted to generate different patterns of UV light from the entire UV spectrum. That is, an initial burst of UV-C light may be followed by longer exposures of UV-A and/or UV-B light. The short, energetic wavelengths of UV-C light are highly effective at sterilizing surfaces but may be limited in their ability to penetrate through obstacles or may decrease in sterilizing power over a distance. UV-A and UV-B light have longer wavelengths that may transmit through barriers and other materials more easily to sterilize the contents of the UV sterilizing pail 10 contained therein. The pattern of UV light expression that may be programmed into the control module 52 may be optimized to provide the most effective level of UVGI. Blue light has been shown to have germicidal effects as well and may be incorporated in any given sterilization routine 5.

The UV light sources 51 may operate at different wavelengths, including 185 nm, which is the length of radiation that produces ozone. Ozone safely interacts with VOC's to effectively eliminate odor and further sterilizes the contents of the UV sterilizing pail 10. While the total effective dose of UV radiation absorbed by the microorganisms may be quite low, the fluence rate (irradiance) over the effective area of sterilization is high enough to kill outright, or render the microorganism sterile and therefore unable to reproduce and cause disease. The fluence (effective UV dose) of the UV light sources 51 may be generated at a rate that is roughly proportional to the power of the UV light source 51 given a stationary distance. The closer the UV light source 51 is to the sterilization target, the greater the fluence will be as well.

The UV sterilizing pail 10 may be adapted for various self-cleaning sterilization routines 5. That is, the UV sterilizing pail 10 may run sterilization routines 5 without any contents stored therein in order to clean the interior surfaces 29 of the pail. While germicidal ultraviolet light, typically around 234-280 nm, is an effective sterilizer, it may be a health hazard to skin and eyes. Far-UVC (207-222 nm) has been shown to efficiently kill pathogens, such as airborne influenzas and coronaviruses, potentially without harm to exposed human tissues. Accordingly, the UV sterilizing pail 10 may be adapted to generate Far-UVC light inside the pail 10, but may also be configured to generate Far-UVC for sterilizing external surfaces 12 of the pail 10, or for safely sterilizing rooms in which the UV sterilizing pail 10 is stored. A UV light source 5 that generates Far-UVC light may be permanently affixed, or modular and attachable to any surface 12, 29 of the UV sterilizing pail 10.

The UV sterilizing pail 10 may include a deodorizer puck assembly (not shown) installed therein. The deodorizer puck assembly may contain a deodorizer such as, but not limited to, an air-freshener or baking soda in order to counteract the odor of the waste stored in the UV sterilizing pail 10. The deodorizer puck assembly may also be adapted to deliver a pretreatment, such as hydrogen peroxide, to the waste deposited therein that may enhance the UV effect of the light generated by the UV sterilizing module 50. The photolysis of hydrogen peroxide caused by the ionization caused by the UV light generates hydroxyl radicals that are powerful oxidizing agents in themselves and contribute to the sterilization process. The deodorizer puck assembly may be replaceable and may include a deodorizer puck assembly attachment (not shown) that interacts with the puck housing. The deodorizer puck assembly attachment may be attached anywhere on the lid assembly 40, housing 60, support structure 70 or base 80 of the UV sterilizing pail 10 through a threaded connection, friction fit, nail, screw, snap fit, hook and loop, adhesive, and the like according to this subject disclosure. The deodorizer puck assembly is described in further detail in U.S. Pat. No. 9,994,393, which is incorporated by reference herein in its entirety into this disclosure. The combination of the deodorizer and the UVGI applied from the UV sterilizing module 50 works to kill microorganisms and reduce malodors.

Figure 17:
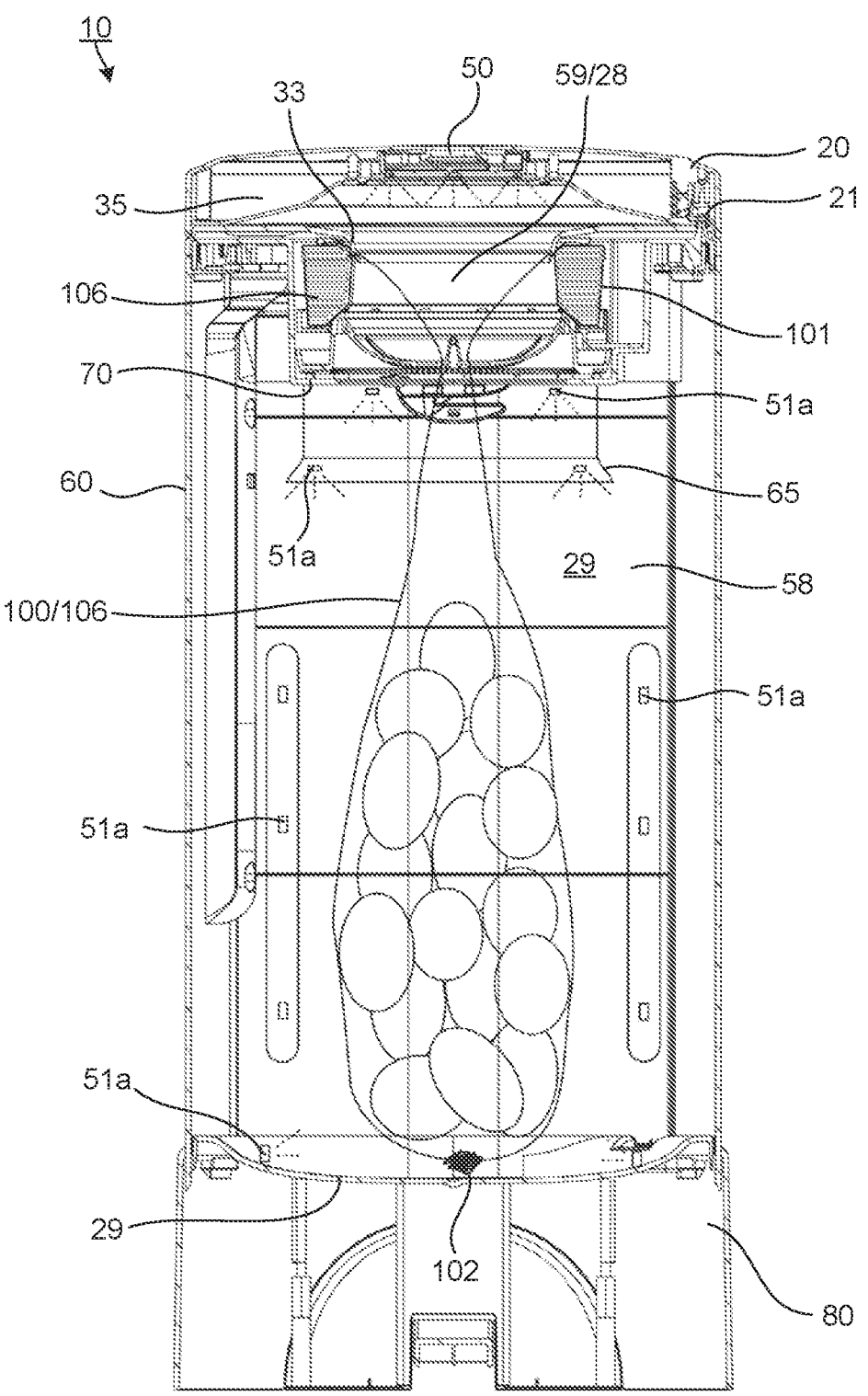
FIG. 17 is a cross-section of the UV sterilizing pail along plane A-A of FIG. 3 with a cassette installed therein, according to an exemplary embodiment of the present subject disclosure.
Figure 18:
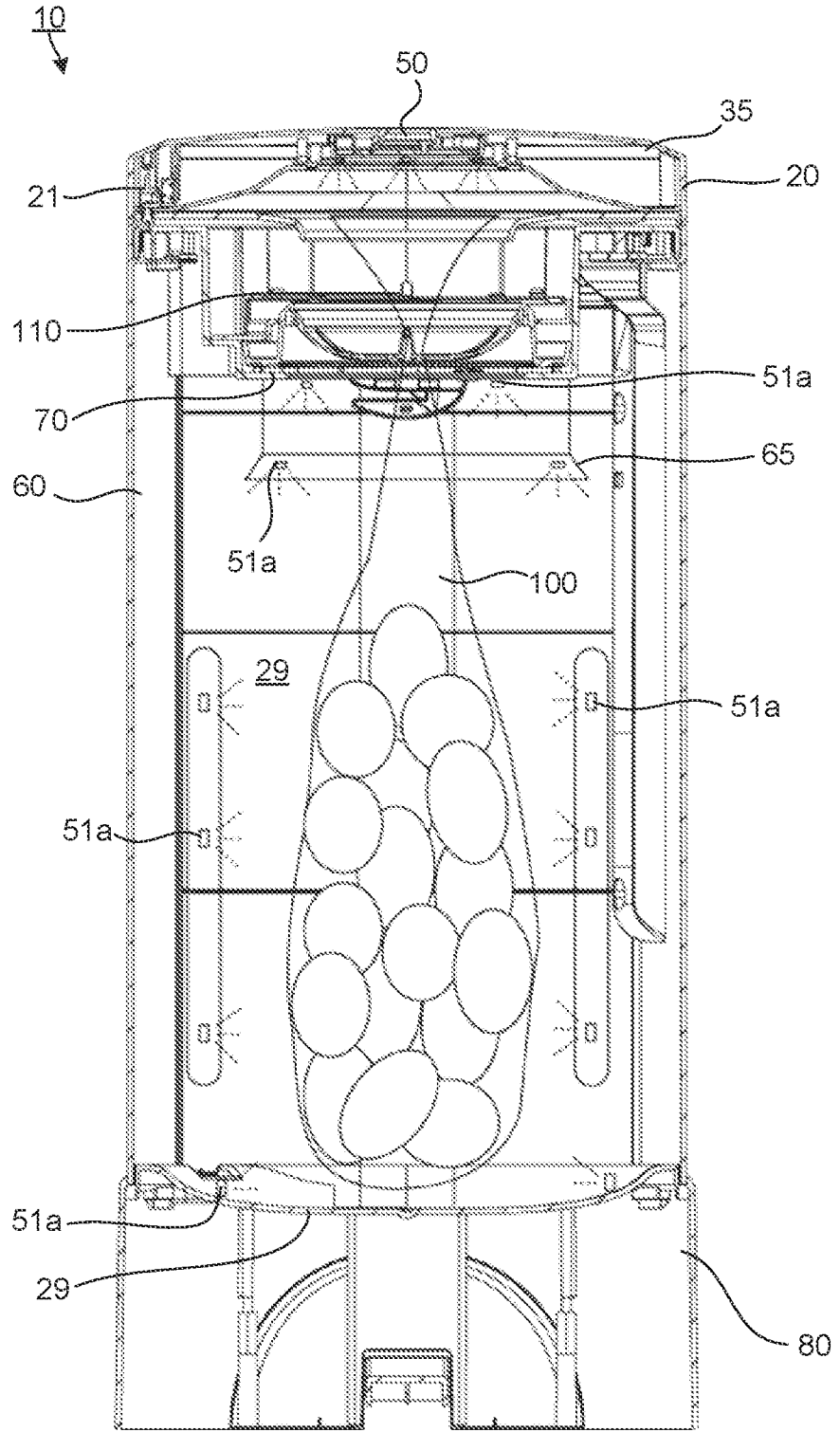
FIG. 18 is a cross-section of the UV sterilizing pail along plane B-B of FIG. 4 with a single use flexible bag installed therein, according to an exemplary embodiment of the present subject disclosure.

FIG. 17 illustrates a cross-section of the UV sterilizing pail 10 along plane A-A of FIG. 3 with the cassette 101 installed therein. FIG. 18 illustrates a cross-section along plane B-B of FIG. 4 with the single use flexible bag 110 installed in the UV sterilizing pail 10. FIG. 17-18 show an exemplary configuration of UV light sources 51 disposed in the UV sterilizing pail 10. As shown in FIG. 17-18, the UV light sources 51 are UV LEDS 51*a* and are configured to generate ultraviolet light for germicidal irradiation (UVGI), sterilization and neutralization of Volatile Organic Compounds (VOCs) that may cause malodor to emanate from the UV sterilizing pail 10. The UV sterilizing module 50 may be disposed in the lid cover 20 with UV LEDS 51*a* extending through the lid cover housing 35 in order to sterilize the portions of the internal lid 30, support structure 70, waste chamber 59 and flexible bag assemblies 100 below the UV LEDS 51*a*. The bottom surface 38 of the lid cover housing 35 may be lined with a reflective surface to enhance the reflection properties of the UV light sources 51. Likewise, various other surfaces of the UV sterilizing pail 10 may be lined with reflective surfaces or mirrors, and/or be formed from inherently reflective materials, in order to enhance, direct and amplify the reflection of the UV light sources 51 disposed throughout such as in the interior storage space 58.

The UV light sources 51 of the UV sterilizing module 50 may adapt any configuration in order to direct the UV light for comprehensive sterilization. The spread angle of the UV lights 51 may be adjusted by changing the shape and properties of the UV light sources 51 or their location on the UV sterilizing module 50. Additional UV light sources 51 may be disposed in the lid cover 20, internal lid 30, support structure 70 or waste chamber 59. The UV light sources 51 disposed in the lid cover 20 are adapted to provide comprehensive sterilization with either the cassette 101 or single use bag assembly 110 installed therein. The UV light sources 51 may be modularly detachable and capable of being secured to any surface 12, 29 of the UV sterilizing pail 10 in a safe and secure manner.

As shown in FIG. 17-18, UV LEDS 51*a* are disposed on an underside of the support structure 70 and on a shoulder 65 disposed on the interior surface 29 of the housing 60. These UV light sources 51 may be pointed downward or at any desired angle to maximize the effectiveness of the UV light for sterilizing the UV sterilizing pail and its contents. UV LEDS 51*a* are disposed in vertical arrays down the interior surfaces 29 of the interior storage space 58 of the housing 60. Additional UV LEDS 51*a* are disposed on/in the interior surfaces 29 of the base 80 and may be configured to shine upward. The effect of this plurality of UV light sources 51 is that the interior surfaces 29 of the housing 60 are bombarded by UV sterilizing light. The UV light generated by the UV light sources 51 also shines onto, and into, the flexible bag assembly 100 installed therein. This sterilizes both the outer and inner surfaces of the flexible bag assembly 100, but also the contents stored inside of the flexible bag assembly 100. The flexible bag assembly 100 may be adapted to transmit UV light, and UV-C light specifically, in order to maximize the penetration of the UV light generated by the UV light sources 51 disposed in the UV sterilizing pail 10. These optimized flexible bag assemblies 100 may increase the penetration and effectiveness of the UV-C light well beyond the normal UV-C transmissive properties of current bags known in the art.

An advantage of the subject disclosure is the ability to effectively transmit UV light through the flexible bag assemblies 100, such that the inner surface of the bag as well as into the contents within the flexible bag assemblies 100 will also be sterilized in an efficient manner. That is, the reduction rate of the transmission of the UV light through the bag film is significantly less employing the material composition of the bag film of the instant subject disclosure than with other commercially available diaper bags. This advantage results in an enhanced kill rate of bacterial within the interior of the flexible bag assemblies 100 from the interior wall deep into the bag film itself.

Figure 19:
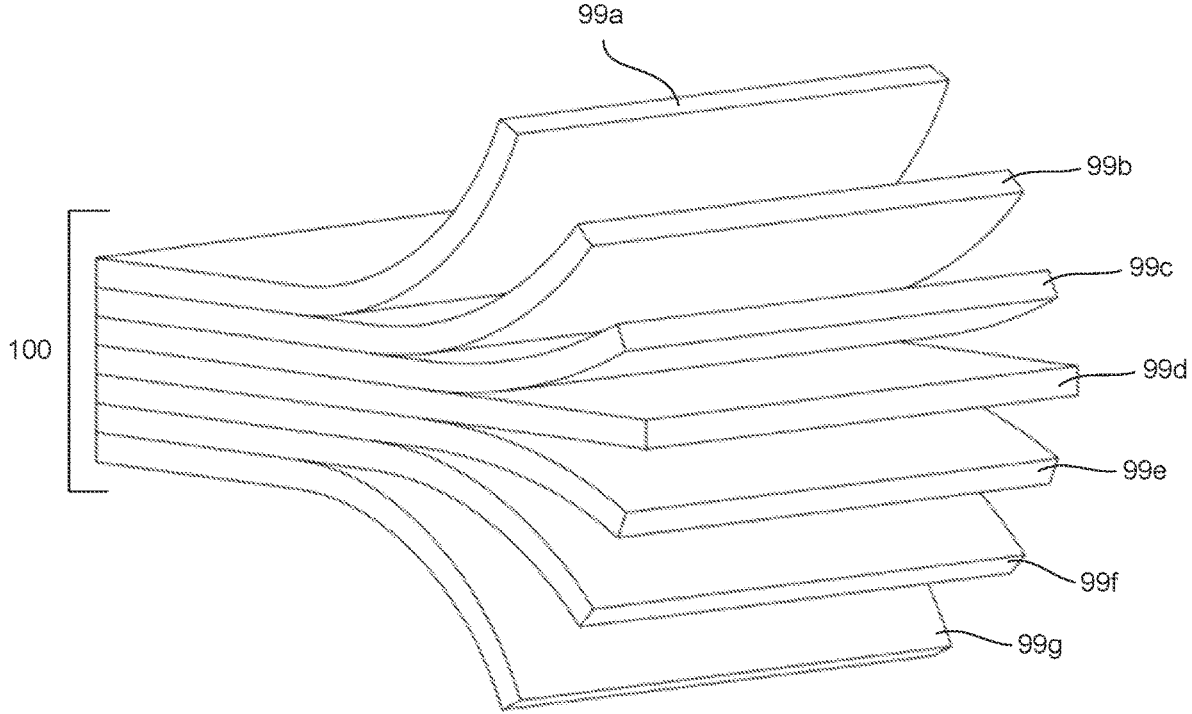
FIG. 19 is a close-up view of the layers of a UV sterilizing bag configuration, according to an exemplary embodiment of the present subject disclosure.

FIG. 19 shows the layered composition of an exemplary flexible bag assembly 100 according to this subject disclosure. The flexible bag assemblies 100 may include multiple layers of flexible material in their construction. One exemplary embodiment of a flexible bag assembly 100 is the single use flexible bag 110 having seven layers. Another exemplary embodiment of the flexible bag assembly 100 is the cassette 101 having flexible tubing 106 that has a seven-layer composition. A first layer 99*a* may be comprised of polyethylene (PE) and/or low-density polyethylene (LDPE), and may include a slip agent or antiblock compound. A second layer 99*b* may be comprised of PE, LDPE, and/or linear low-density polyethylene (LLDPE). The second layer 99*b* may include a pigment, slip agent or antiblock compound. A third layer 99*c* may be comprised of an anhydride-modified, LLDPE resin. A fourth layer 99*d* may be comprised of an ethylene vinyl alcohol (EVOH) copolymer. A fifth layer 99*e* may be comprised of an anhydride modified, LLDPE resin. A sixth layer 99*f* may be comprised of PE, LDPE and/or LLDPE and may include a pigment, slip agent or antiblock compound. A seventh layer 99*g* may be comprised of PE, LDPE, and may include a slip agent or antiblock compound.

Additionally, the flexible bag assemblies 100 may be comprised completely or partially of one or more biopolymers, such as starch, cellulose derivatives, natural rubbers, polyimides, bio-monomers (polyimides, polyurethanes, polybutylene succinate (PBS), Polyhydroxyalkanoates (PHAs), Poly(3-hydroxybutyrate-co-3hydroxyvalerate)

(PHBV), bio-based PE, bio-based polyethylene terephthalate (Bio-PET), polylactic acid (PLA), and the like according to this subject disclosure.

Fluorinated Ethylene Propylene (FEP) is one material that exhibits excellent transmission of UV light. FEP is used for components in the Hubble Space Telescope and the International Space Station because of its robust material properties that are able to withstand the harsh demands of outer space. FEP tubing may transmit UV light effectively without suffering the degradation caused by photo-oxidation and unwanted polymer cross-linking associated with the effects of UV light on other consumer plastic products. FEP may be the primary component in any layer 99*a-g* of the flexible bag assemblies 100.

The layers 99*a-g* of the flexible bag assemblies 100 may be of interchangeable and may be layered in any order. The flexible bag assemblies 100 may have different layer configurations, or number of layers, using the above listed materials, or similar. For example, the flexible bag assembly 100 may be formed of eleven layers, nine layers, five layers (99*b-f*), three layers (99*b-d*), or a single layer, and the like according to this subject disclosure.

The flexible bag assemblies 100 may be adapted to effectively transmit UV light, such that the inner surface of the bag 100 and contents of the flexible bag assemblies 100 will also be sterilized. The ability of UV light, especially UV-C light to penetrate materials is dependent, in large part, on the chemical and structural composition of the materials. In order to create flexible bag assemblies 100 capable of effectively transmitting UV light, it is necessary to balance the chemical contents of the materials used therein. Stabilizer, blockers, absorbers, antioxidants, pigments and other additives may be used in the flexible bag assemblies 100 such that they do not interfere with the transmission of UV light. In one embodiment, all layers 99*a-g* of the flexible bag assembly 100 may be clear (without pigment) in order to promote the transmission of UV light into the flexible bag assembly 100.

One of the advantages to a multi-layer bag relative to the transmission of UV light is the relative thinness of the individual layers 99*a-g* that the UV light must pass through. The layers 99*a-g* of the flexible tubing 106 of the cassette may be substantially between 9-30 microns in order to minimize the overall gauge width of the flexible tubing 106 that UV light must pass through in order to reach the inside of the bag 100. In one embodiment, a PE layer of the flexible tubing 106 of the cassette may have a width of 21 microns. Additionally, the layers 99*a-g* of the single use flexible bag 110 may be substantially between 14-45 microns in order to minimize the overall gauge width of the single use flexible bag 110 that UV light must pass through in order to reach the inside of the bag 100. In one embodiment, a PE layer of the single use flexible bag 110 may have a width of 30 microns.

The layers 99*a-g* of the flexible bag assemblies 100 may include a bio-assimilator compound, such as ECLIPSE™. Traditional plastic materials like PE may be difficult to degrade in the environment. A bio-assimilator is a compound that degrades plastic to a molecular weight that can be consumed by living organisms. This is a final and conclusive stage of plastic biodegradation that leaves behind no microplastic remnants. The addition of a bio-assimilator to polyolefins like PE can be tailored to ensure a useful-life performance before degrading according to a set time-table. For example, a bio-assimilator may be added to any of the layers 99*a-g* with a simple inclusion rate between 0.01-2% concentration (w/w) in the masterbatch or at any time during the finished film production process. Additionally, a bio-assimilator may comprise between 0.01-10% concentration of the plastic formulation used to manufacture the flexible bag assemblies 100. In one embodiment, the flexible bag assembly 100 may be manufactured to contain approximately 1% of the final weight of the flexible bag assembly. The flexible bag assembly 100 may be adapted to degrade between 1 and 60 months. In one embodiment the flexible bag assembly 100 may be adapted to degrade between 18-24 months. In another embodiment the flexible bag assembly may be adapted to degrade in approximately 36 months.

An antimicrobial such as Molybsan™, Liquid Guard™, GermGuard™, Supra-Guard™, or the like having a comparable chemical composition, may be included in the flexible bag assemblies 100 as an additive or as a coating on one or more of the layers 99*a-g*. Additional additives incorporated into the flexible bag assemblies 100 may include stabilizers, antistatic agents, flame retardants, plasticizers, lubricants, antiblock and slip agents, curing agents, foaming agents, catalyst deactivators, nucleators, biocides, pigments, soluble azocolorants, fillers, fiber reinforcements, and the like according to this subject disclosure. Additives in the flexible bag assemblies may be organic, inorganic or a combination of both types of compounds.

The additives used in the flexible bag assemblies 100 may be optimized for the transmission of UV light. For example, non-migratory slips reduce film clarity more than primary or secondary amides and may be avoided. The refractive index of the additive particles is also important, as differences between the additive particles and the surrounding polyolefin determine the additives' impact on clarity or haze. Haze is lower as the refractive index of the additive approaches that of the polymer. The refractive index of polyethylene is 1.5 and additives may be chosen that most closely match the refractive index of the layer 99*a-g* in which the additive is used. Additionally, the number of additive particles and the particle size distribution of the additive may be optimized to maximize the transmission of UV light through the flexible bag assembly 100.

The optical properties of PE-based films vary between clear (transparent), partially opaque (translucent) or opaque depending on the thermal history and film thickness of the material. LDPE has the greatest transparency, LLDPE slightly less, while high density polyethylene (HDPE) has the least transparency. Transparency is reduced by crystallites if they are larger than the wavelength of the transmitted light.

In the field of optics, transparency is the physical property of allowing light to pass through a material without appreciable scattering of light. A transparent material is made up of components with a uniform index of refraction. When dealing with the macroscopic scale, where the dimensions investigated are much larger than the wavelengths of light, photons follow Snell's Law. Translucency is the physical property describing the passage of light through a material made up of components with different indices of refraction. Translucency implies that the behavior of the photons may not necessarily follow Snell's Law, as the photon may be scattered at either of the two interfaces of the material, or internally where there is a change in the index of refraction. The flexible bag assemblies 100 may be transparent or translucent and adapted to maximize the transmission of UV light.

When light encounters a material, it is either reflected, absorbed or transmitted through the material. These interactions depend on the wavelength of the light and the nature of the material. Some materials such as borosilicate glass, quartz or clean water transmit most of the light shined thereon without much reflection. These materials are called optically transparent. Many liquids and aqueous solutions are highly transparent due to the absence of structural defects and the molecular structure of these liquids. Materials that do not transmit light are called opaque.

In regards to the absorption of light in the ultraviolet and visible (UV-Vis) portions of the spectrum, absorption depends on the electron orbitals of the atoms that comprise the material through which the light is traveling. Quantum selection rules describe the allowable transition of electrons between orbitals and whether the electron may absorb a quantum of light (photon) of a specific frequency. For example, in most glasses, there are no available electron energy orbitals above that of the steady state atomic orbital that an electron could transition to without violating selection rules, and therefore, there is no appreciable absorption of visible light in pure glasses.

When photons come in contact with the valence electrons of an atom several things may occur. The atom or molecule may absorb the photon and some of the energy may be lost through luminescence, fluorescence and phosphorescence. The atom or molecule may absorb the photon with some reflection or scattering of the light, or if the molecule cannot absorb the energy of the photon, the photon continues on its path. This results in transmission, absent some other absorption mechanism coming into play. When light strikes an object, it usually not a single frequency (wavelength), but many. Most of the time, some combination of the above listed events will occur. Transmission depends on the above listed variables and largely on the range of energies that the material may absorb. Most glasses, for example, block UV light. The electrons in the glass absorb the energy of the photons in the UV range while ignoring the weaker energy of photons in the visible light. As mentioned above, some special glasses such as borosilicate glass or quartz are UV-permeable and thus allow a high transmission of UV light.

Regarding the scattering of light, the most important factor is the length scale of the structural features of the incident material relative to the wavelength of the light being scattered. Primary material considerations include whether the atoms of molecules exhibit crystalline structure, the presence of "scattering centers": including fluctuations in density or composition, grain boundaries, crystallographic defects and microscopic pores, and in organic materials fibers and cell structures and boundaries. The flexible bag assemblies 100 may be manufactured to minimize the presence of scattering centers in the material.

Most insulators (dialectic materials) are held together by ionic bonds and do not have free conduction electrons, resulting in only a small fraction of reflected light. The remaining frequencies are free to propagate (transmission). Polyethylene consists of nonpolar, saturated, high molecular weight hydrocarbons. The individual macromolecules are not covalently linked, although the curing process used with certain thermosets may result in covalent bonding and cross-linking between the molecules. PE is partially crystalline, and this property influences the directionality of the transmission of incoming light. The addition of additives, such as pigments, in the manufacturing of PE films introduce color centers that absorb light or scattering centers that interrupt the light traveling through the film. Ideally, the PE materials used in the construction of the flexible bag assemblies 100 will be as free of such additives as possible. Construction of the flexible bag assemblies 100 must balance the physical use-constraints of the flexible bag assemblies 100 with those properties that maximize optical transparency and the transmission of high energy, high frequency, small wavelength UV light.

The surface of the flexible bag assemblies 100 may be non-ionic and inert to minimize reactivity and denaturation. The composition of the flexible bag assemblies 100 may be polarized to only allows certain desirable wavelengths through the flexible bag assemblies 100. The flexible bag assemblies 100 may have an optimized geometry for the transmission of UV light. The flexible bag assemblies may have an optimized chemical formulation and molecular structure to maximize the transmission of UV light. The layers 99*a-g* of the flexible bag assemblies may have a coordinated geometry between the various layers 99*a-g* in order to introduce UV transmission pathways through the layers 99*a-g* exhibiting a high level of optical transparency. The surface layers 99*a*, 99*g* may have an optimized geometry to promote the transmission of UV light. The surface layers may exhibit natural patterns, symmetry, periodic tiling, spirals, waves, foam structure and the like according to this subject disclosure. Depending on the process used in the manufacturing process, this optimized geometry, such as periodic windows or channels of high optical transparency and clarity, may be repeated throughout the length and width of the flexible bag assemblies 100.

Figure 20:
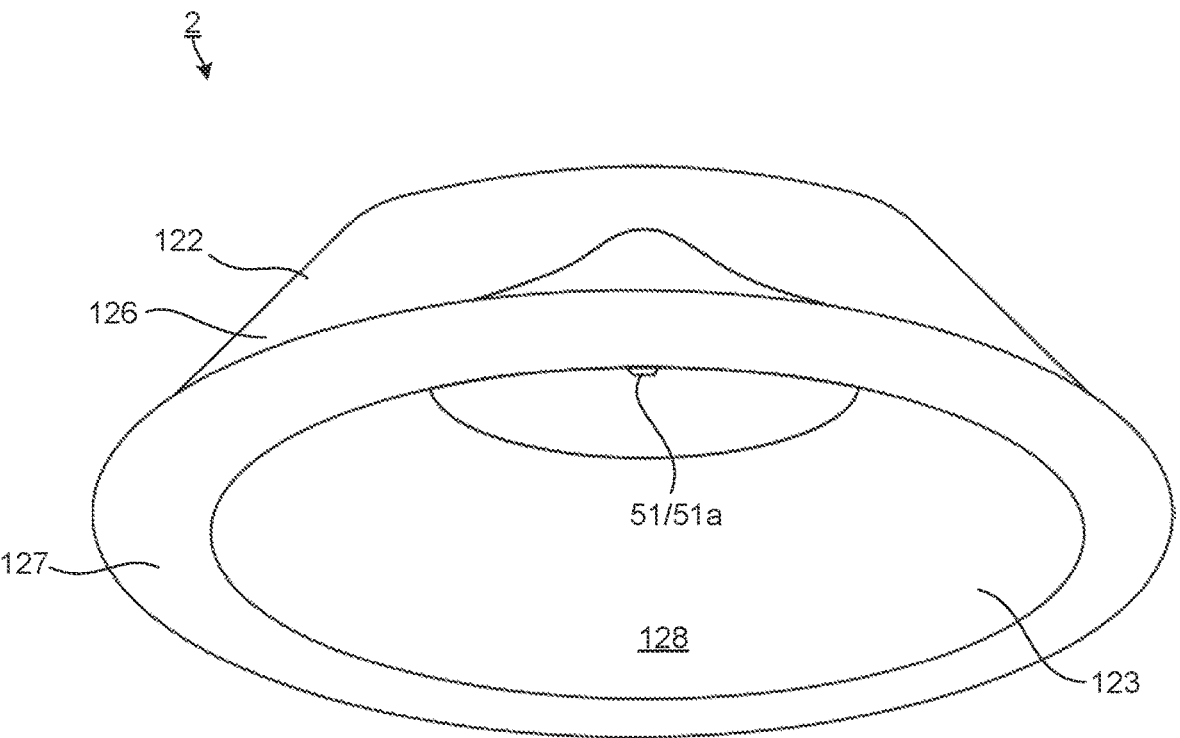
FIG. 20 is a front perspective view of a UV sterilizing puck, according to an exemplary embodiment of the present subject disclosure.

FIG. 20 is a front perspective view of the UV sterilizing puck 2. The UV sterilizing puck may include a puck housing 122, a circuit on an electronic control unit, a power supply, at least one UV light source 51 and an attachment mechanism 124 (FIG. 21) for attaching the UV sterilizing puck 2 to a surface. The UV light generated by the UV sterilizing puck 2 may last for a given duration long enough to sterilize the interior surfaces 29 of the UV sterilizing pail 10 and contents stored therein. Alternatively, the UV sterilizing puck 2 may be adapted for use with comparable diaper pails, waste receptacles or containers.

As shown in FIG. 20, the UV sterilizing puck 2 may have a recessed surface 128 disposed on the bottom of the puck housing 122. The UV Light source 51, as shown a UV LED 51*a*, may be disposed at the top of the recessed surface 128 or may be disposed at any point along the interior wall of the recessed surface 128. The recessed surface 128 may be a reflective surface 123. The recessed surface 128 may be contoured at a predetermined angle to encourage reflectivity of the UV light. The recessed surface 128 may be reflective due to the natural properties of the material used to form the puck housing, or the recessed surface may be provided with a reflective coating for directing or amplifying the UV-C light generated by the UV sterilizing puck 2. The puck housing 122 may be comprised of thermoplastic, various elastane materials, silicone, metal and metal alloys, ceramics, and/or any other suitable material according to this subject disclosure.

The puck housing 122 may contain the electronic control unit on a circuit board with the UV light source 51 and the power supply. The puck housing 122 may also contain a communication transceiver 46, a timer 47 and at least one accelerometer 41. The communication transceiver 46 may be configured to interact with a remote control or an application on a mobile phone for remotely activating or controlling the UV sterilizing puck 2. The power supply may be a rechargeable battery or at least one replaceable battery. The UV sterilizing puck 2 may have a USB assembly that is configured to charge the rechargeable battery. The UV sterilizing puck 2 may be powered by a solar power and a solar panel may be disposed on the diaper pail or the puck housing. The UV sterilizing puck 2 may include an indicator light 24 that indicates that the UV sterilizing puck 2 is actively generating UV light.

The UV sterilizing puck 2 may be activated manually by a power button switch disposed on an outer surface 126 or a perimeter 127 of the puck housing 127. When the UV sterilizing puck 2 is activated by the power button switch, a timer may be activated that allows a user to close the cover lid 20 before the sterilization routine 5 begins. Use of the power button on the puck may also put the UV sterilizing puck 2 in an "active" state that will begin the sterilization process when the lid 20 is closed. The UV sterilizing puck 2 may also be configured to automatically begin the sterilization process when the lid 20 is closed. Different sterilization programs or routines may be programed into the electronic control unit of the UV sterilizing puck 2.

Because of the damage that the UV-C light may cause to a viewer's eyes or skin, it is of crucial importance that the light generated by the UV sterilizing puck 2 is contained. The accelerometer 41 may be one mechanism for ensuring the safe operation of the UV sterilizing puck 2. The accelerometer 41 of the UV sterilizing puck 2 may be a multi-axis sensor that measures the acceleration due to gravity in more than one direction. A tri-axis accelerometer 41 may be used to detect the position of the UV sterilizing puck 2 in three dimensions so that the puck 2 may be configured to only operate in certain resting positions. For example, the UV sterilizing puck 2 may be configured to only operate when it is resting substantially parallel to the surface supporting the UV sterilizing pail 10. This would correspond to the lid cover 20 being in a closed position such that the UV light is safely contained within the pail 10. The accelerometer 41 in the UV sterilizing puck 2 may recognize when the cover lid 20 is open because the UV sterilizing puck 2 would be substantially orthogonal to the horizon, and consequently the UV sterilizing puck 2 would not activate. Other sensors may be disposed on the UV sterilizing puck 2 or included therewith in order to promote safe operation of the UV sterilizing puck 2.

Figure 21:
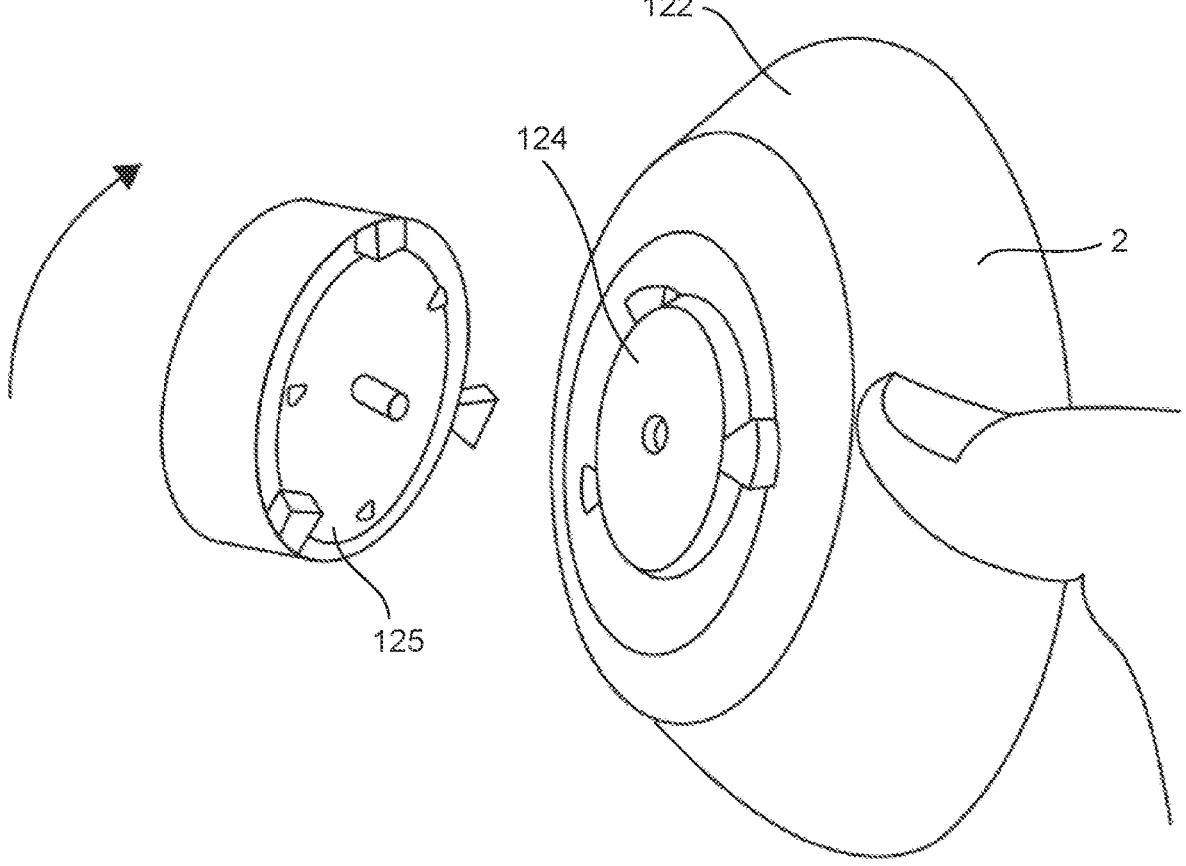
FIG. 21 is a front perspective view of a UV sterilizing puck and pail adapter, according to an exemplary embodiment of the present subject disclosure.

As shown in FIG. 21, the UV sterilizing puck 2 may include an attachment mechanism 124. The attachment mechanism 124 may be configured to interact directly with a complementary adapter 125 that may then be affixed to the lid cover 20 or another suitable surface. Possible attachment configurations include friction fit, snap fit, hook and loop, locking fit, adhesive and the like according to this subject disclosure. As shown in FIG. 21, the attachment mechanism 124 may be keyed to interact with the adapter 125. The attachment mechanism 124 is a female connector that mates with a complementary male portion on the adapter 125 through a keyed fit. The female connector may be a keyed recess. The male connector on the adapter 125 may be inserted into the keyed recess and rotated in order to lock the UV sterilizing puck 2 within the keyed recess. This configuration may be reversed such that the attachment mechanism 124 on the puck housing 122 is the male connector and the adapter 125 is the complementary female connector. The UV sterilizing puck 2 may include both portions of the attachment mechanism 124 in order to facilitate the installation of the UV sterilizing puck 2 in other diaper pails or containers.

Figure 22:
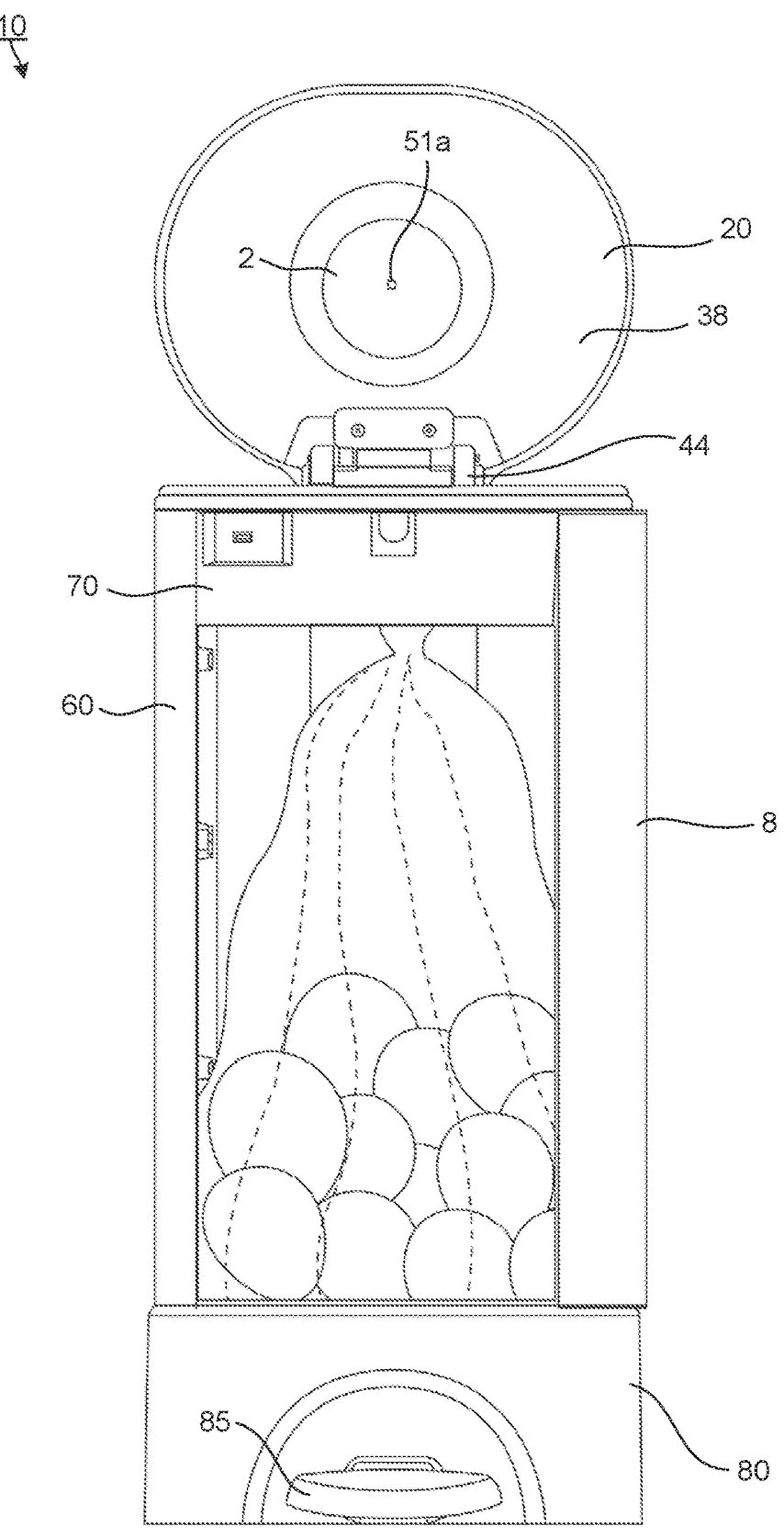
FIG. 22 is a front view of a UV sterilizing pail with a lid cover and a housing door shown in an open position with a UV sterilizing puck and a flexible bag installed therein, according to an exemplary embodiment of the present subject disclosure.

FIG. 22 is a front view of the UV sterilizing puck 2 installed in a UV sterilizing pail 10. The attachment mechanism 124 and adapter 125 are used to releasably attach and secure the UV sterilizing puck 2 to the bottom surface 38 of the cover lid 20 in order to sterilize the UV sterilizing pail 10.

Figure 23:
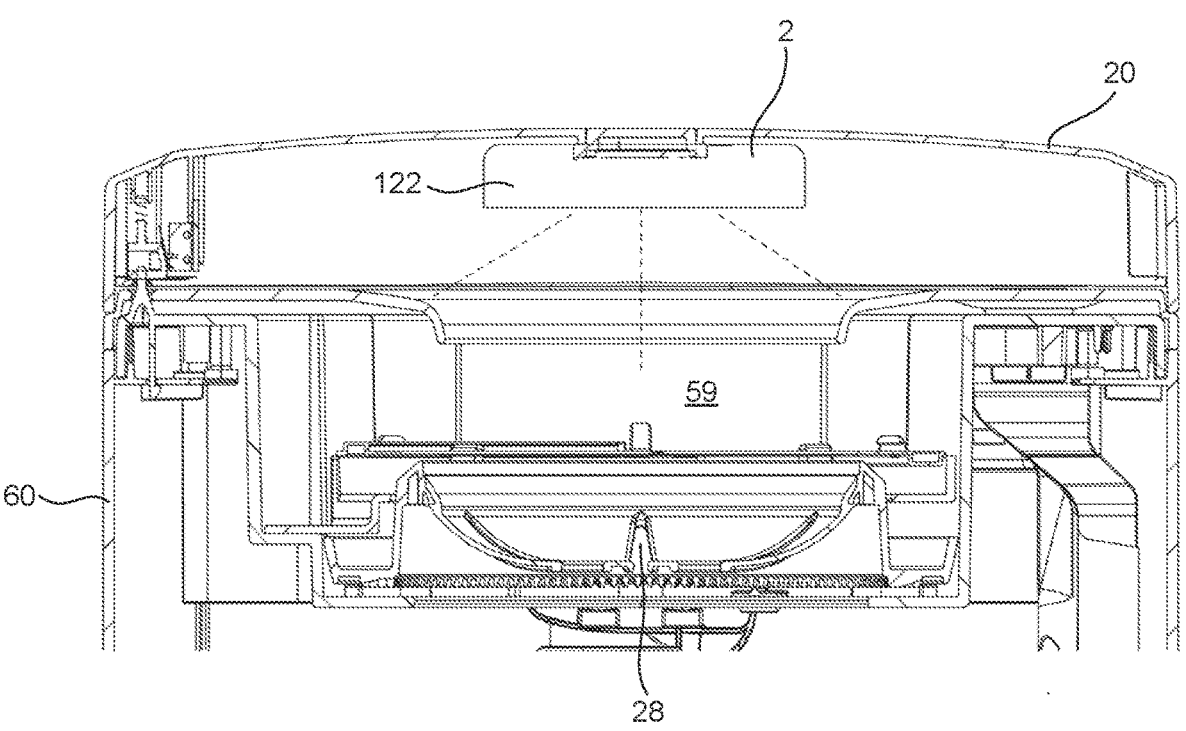
FIG. 23 is a cross-section of the UV sterilizing pail along plane B-B of FIG. 4 with a UV sterilizing puck installed therein, according to an exemplary embodiment of the present subject disclosure.

FIG. 23 is a partial cross-section view of the UV sterilizing pail 10 with the UV sterilizing puck 2 installed therein. When the cover lid 20 is closed, the UV-C sterilizing puck 2 may be activated to generate UV-C light and engulf a directed portion of, or the entirety of the internal lid 30, support structure 70, the flexible bag assembly 100 and the opening 28 to the interior storage space 58 disposed in the housing 60.

The UV sterilizing puck 2 may include a deodorizer assembly. The deodorizer assembly may be disposed on the exterior surface 126 of the puck housing 122. The deodorizer assembly may contain a deodorizer such as, but not limited to, an air-freshener or baking soda in order to counteract the odor of the waste stored in the diaper pail. The deodorizer assembly may be replaceable and may include a deodorizer assembly attachment that interacts with the puck housing 122 or a complementary deodorizer assembly dock disposed on the puck housing 122. The deodorizer assembly dock may be a channel in the perimeter of the puck housing 122 with a locking feature. The deodorizer assembly attachment may be a rail that slides within the channel for a locking fit on the puck housing 122. Other attachment means are contemplated including, but not limited to, a threaded connection, friction fit, nail, screw, snap fit, hook and loop, adhesive, and the like according to this subject disclosure.

As employed in this specification and annexed drawings, the term "or" is intended to mean an inclusive "or" rather than an exclusive "or." Moreover, articles "a" and "an" as used in the subject specification and annexed drawings should generally be construed to mean "one or more" unless specified otherwise or clear from context to be directed to a singular form.

What has been described above includes examples that provide advantages of the subject disclosure. It is, of course, not possible to describe every conceivable combination of components or methodologies for purposes of describing the subject disclosure, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The illustrations and examples provided herein are for explanatory purposes and are not intended to limit the scope of the appended claims. It will be recognized by those skilled in the art that changes or modifications may be made to the above described embodiment without departing from the broad inventive concepts of the invention. It is understood therefore that the invention is not limited to the particular embodiments described herein but is intended to cover all modifications and changes within the scope and spirit of the invention.

What is claimed:

1. A method of sanitizing a diaper pail, comprising:
   providing a container having a housing and a lid assembly;
   integrating a support structure into the container disposed between the housing and lid assembly that is adapted to receive two different types of flexible bag assemblies, wherein the support structure has a first stationary support member having a first support surface dimensioned to seat and secure a first bag assembly, and a second stationary support member having a second support surface vertically offset from the first support surface and that extends horizontally below the first support surface dimensioned to seat and secure a cassette of a second bag assembly;
   opening a cover lid of the lid assembly to deposit an article of waste into a waste chamber disposed in the support structure;
   closing the cover lid;
   engaging at least one multi-axis sensor by detecting that the cover lid is closed and substantially parallel to a surface supporting the diaper pail; and
   directing an ultraviolet (UV) light downwardly from a bottom surface of the lid assembly onto an interior surface of the diaper pail when the at least one multi-axis sensor is engaged.

2. The method of claim 1, further comprising the steps of:
   after engaging the at least one multi-axis sensor, activating a UV light module to control the UV light; and
   running a sanitization routine stored in a memory module of the UV light module.

3. The method of claim 1, wherein the at least one multi-axis sensor is disposed on the lid assembly.

4. The method of claim 3, further comprising: placing a second sensor on a door that opens into an interior storage space of the housing.

5. The method of claim 2, wherein the UV light module is disposed on the cover lid.

6. The method of claim 1, wherein the UV light has a wavelength within the UV-C spectrum.

7. The method of claim 1, further comprising: placing a second UV light in the housing.

8. The method of claim 7, wherein the second UV light directs UV light onto and through a flexible bag assembly installed in the housing to sanitize the article of waste stored therein.

9. The method of claim 8, wherein the second bag assembly is the cassette for dispensing flexible tubing.

10. The method of claim 8, wherein the first bag assembly is a flexible tubing connected to a frame.

11. A method of sanitizing a diaper pail having a housing and a lid assembly with an ultraviolet (UV) light, comprising:
   integrating a support structure into the diaper pail having an opening adapted to receive two different types of flexible bag assemblies, the support structure having a first stationary support member having a first support surface dimensioned to seat and secure a first bag assembly, and a second stationary support member having a second support surface vertically offset from the first support surface and that extends horizontally below the first surface dimensioned to seat and secure a cassette;
   inserting an article of waste into the diaper pail through the opening in the support structure positioned within a housing of the diaper pail;
   sealing the diaper pail from an external environment to prevent UV light from emanating therefrom;
   activating a UV sanitizing routine stored in a UV light module that is connected to at least one UV light source, wherein the UV sanitizing routine is activated by verifying that a multi-axis lid sensor is engaged by detecting that the lid is closed and substantially parallel to a surface supporting the diaper pail;
   irradiating an interior surface of the diaper pail with the UV light directed downwardly from a bottom surface of the lid assembly; and
   deactivating the UV sanitizing routine after a predetermined time period.

12. The method of claim 11, wherein the diaper pail comprises:

the housing having an upper end and a lower end;
a base attached at the lower end; and
the lid assembly pivotally attached by a hinge to the upper end, the lid assembly having:
a lid cover; and
an internal lid.

13. The method of claim 12, further comprising: positioning at least one sensor on the diaper pail that is engaged for the UV light module to activate and run the UV sanitizing routine.

14. The method of claim 12, wherein the UV sanitizing routine further comprises the steps of:

verifying that a door sensor is engaged when a door of the housing is closed;
activating the UV light source for the predetermined time period; and
ceasing operation of the UV sanitizing routine immediately if the lid sensor or the door sensor is disengaged.

15. The method of claim 12, further comprising an additional UV light source disposed in the housing.

16. The method of claim 15, wherein the additional UV light source directs UV light onto and through a tubing of the flexible bag assembly installed on the support structure to sanitize the contents stored therein.

17. A method of cleaning a diaper pail comprising:

providing a container having a housing and a lid assembly;
integrating a support structure into the container having an opening adapted to receive two different types of flexible bag assemblies, the support structure disposed between the housing and the lid assembly;
installing at least one of the flexible bag assembly on a first stationary support member or a second stationary support member of the support structure, wherein the second stationary support member extends horizontally below and is vertically offset from the first stationary support member;
pulling a flexible tubing from the flexible bag assembly through the opening in the support structure;
inserting an item of waste in the flexible tubing of the flexible bag assembly;
closing a cover lid of the lid assembly, the cover lid containing at least one ultraviolet (UV) light source and at least one multi-axis sensor that detects a position of the lid assembly; and
directing UV light from the UV light source downwardly from a bottom surface of the lid assembly onto the item of waste stored in the diaper pail, wherein the UV light source is activated only when the at least one multi-axis sensor detects that the cover lid is resting substantially parallel to a surface supporting the diaper pail.

18. The method of claim 17, further comprising the step of: engaging the at least multi-axis one sensor before directing the UV light.

19. The method of claim 17, further comprising: providing an additional UV light source in the housing.

20. The method of claim 19, wherein the additional UV light source directs the UV light onto and through the flexible tubing of the flexible bag assembly installed in the diaper pail to sanitize the contents stored therein.

21. The method of claim 17, wherein the flexible bag assembly on the second stationary support is a cassette for dispensing the flexible tubing.

22. The method of claim 17, wherein the flexible bag assembly on the first stationary support is the flexible tubing connected to a frame.

23. A method of sanitizing a diaper pail having a housing and a lid assembly with an ultraviolet (UV) light disposed therein, comprising:

installing a bag assembly into the diaper pail having a support structure integrated and positioned within a housing, the support structure having an opening adapted to receive two different types of flexible bag assemblies, the support structure having a first stationary support member having a first support surface dimensioned to seat and secure a first bag assembly, and a second stationary support member having a second support surface vertically offset from the first support surface and that extends horizontally below the first support surface dimensioned to seat and secure a cassette;
inserting an article of waste into a flexible portion of the bag assembly;
sealing the diaper pail to prevent the UV light from escaping outside of the diaper pail to an external environment;
activating a UV sanitizing routine that controls the UV light, wherein the UV sanitizing routine is activated by verifying that a multi-axis lid sensor is engaged by detecting that the lid is closed and substantially parallel to a surface supporting the diaper pail; and
irradiating an interior surface of the diaper pail with the UV light directed downwardly from a bottom surface of the lid assembly.

24. The method of claim 23, wherein the first bag assembly is a flexible tubing connected to a frame.

25. The method of claim 23, wherein the second bag assembly is the cassette for dispensing flexible tubing.

* * * * *